United States Patent [19]

Jones et al.

[11] Patent Number: 5,973,072
[45] Date of Patent: *Oct. 26, 1999

[54] POLYMERIC VEHICLES WHICH INCLUDE A PHENOLIC URETHANE REACTIVE DILUENT

[75] Inventors: Frank N. Jones, Ann Arbor, Mich.; Vijay Swarup, Houston, Tex.; Ramachandran P. Subrayan, Ypsilanti, Mich.; Suru Zhang, Highland Park, N.J.

[73] Assignee: Exxon Chemical Patents, Inc., Baytown, Tex.

[*] Notice: This patent is subject to a terminal disclaimer.

[21] Appl. No.: 08/621,177

[22] Filed: Mar. 21, 1996

Related U.S. Application Data

[60] Provisional application No. 60/002,063, Aug. 9, 1995.

[51] Int. Cl.$^6$ .............................. C08L 75/04; C08L 75/06; C08L 75/12; C08L 61/24; C08L 61/28; C08L 61/32; C08G 18/32; C08G 18/38; C08G 18/46; C07C 69/88; C07C 271/12; C07C 271/26

[52] U.S. Cl. ................. 525/123; 252/182.2; 252/182.23; 252/182.24; 252/182.26; 252/182.28; 525/124; 525/131; 525/440; 525/452; 525/453; 525/454; 525/456; 525/457; 525/458; 525/519; 525/520; 525/523; 525/528; 525/533; 525/534; 525/437; 525/441; 525/442; 525/443; 528/45; 528/49; 528/73; 528/75; 528/80; 528/81; 528/85; 528/149; 528/176; 528/206; 528/208; 528/209; 528/210; 528/250; 528/266; 560/24; 560/25; 560/26; 560/67; 560/71; 560/74; 560/75; 560/115; 560/130; 560/143; 560/157; 560/158; 560/330; 560/335

[58] Field of Search ...................................... 525/452, 453, 525/519, 520, 123, 124, 131, 440, 454, 456, 457, 458; 528/49, 73, 80, 81, 85, 45, 75, 149, 176, 206, 208, 209, 210, 250, 266; 560/24, 25, 26, 67, 71, 74, 75, 115, 130, 143, 157, 158, 330, 335; 252/182.2, 182.23, 182.24, 182.26, 182.28

[56] References Cited

U.S. PATENT DOCUMENTS

| | | | |
|---|---|---|---|
| 3,409,579 | 11/1968 | Robins | 523/143 |
| 3,789,044 | 1/1974 | Taft et al. | 528/73 |
| 3,836,491 | 9/1974 | Taft et al. | 528/53 |
| 4,031,068 | 6/1977 | Cantor | 525/351 |
| 4,130,549 | 12/1978 | Ueno et al. | 528/93 |
| 4,331,782 | 5/1982 | Linden | 525/173 |
| 4,343,839 | 8/1982 | Blegan | 427/340 |
| 4,365,039 | 12/1982 | Blegan | 524/773 |
| 4,374,167 | 2/1983 | Blegan | 428/141 |
| 4,374,181 | 2/1983 | Blegen | 428/423.3 |
| 4,877,838 | 10/1989 | Toman | 525/107 |
| 4,888,441 | 12/1989 | Calbo, Jr. et al. | 560/198 |
| 4,922,002 | 5/1990 | Calbo, Jr. et al. | 528/286 |
| 5,019,100 | 5/1991 | Hennink et al. | 524/361 |
| 5,166,289 | 11/1992 | Yezrielev et al. | 525/443 |
| 5,210,155 | 5/1993 | Yezrielev et al. | 525/442 |
| 5,235,006 | 8/1993 | Jones et al. | 525/510 |
| 5,239,018 | 8/1993 | Yezrielev et al. | 525/418 |
| 5,322,884 | 6/1994 | Wellman et al. | 524/601 |
| 5,326,831 | 7/1994 | Yezrielev et al. | 525/437 |
| 5,334,652 | 8/1994 | Wellman et al. | 524/601 |
| 5,334,671 | 8/1994 | Yezrielev et al. | 525/443 |
| 5,453,469 | 9/1995 | Yezrielev et al. | 525/418 |
| 5,458,920 | 10/1995 | Yezrielev et al. | 427/385.5 |
| 5,681,906 | 10/1997 | Yezreilev et al. | 525/450 |

FOREIGN PATENT DOCUMENTS

| | | |
|---|---|---|
| 0419088 | 3/1991 | European Pat. Off. |
| 2809768 | 9/1978 | Germany . |
| 05155840 | 6/1993 | Japan . |
| 5155840 | 6/1993 | Japan . |
| 1290848 | 9/1972 | United Kingdom . |

OTHER PUBLICATIONS

Swarup et al., "Thermoset Coating Compositions Having Improved Hardness," Research Disclosure No. 374, pp. 446–457, (Jun. 1995), Kenneth Mason Publications, Ltd., Hampshire, England.

Stumpe et al., "Deactivation of Excited States in Polyurethanes by Energy Transfer to Salicylic Acid Derivatives and its Application to the Photo–stabilisation of Polyurethanes", Polymer Degradation and Stability 17 (1987) 103–115.

Stumpe et al.; "Deactivation of Excited States in Polyurethanes by Energy Transfer to Salicylic Acid Derivatives and its Application to the Photo–stabilisation of Polyurethanes"; *Polymer Degradation and Stability*; Elsevier Applied Science Publishers Ltd.; England; vol. 17; 1987; pp. 103–115.

*Primary Examiner*—Rabon Sergent
*Attorney, Agent, or Firm*—Fitch, Even, Tabin & Flannery

[57] ABSTRACT

The present invention is directed to a polymeric vehicle, the formulated coating composition and a coating binder made from the polymeric vehicle and a method for making the polymeric vehicle where the polymeric vehicle includes a phenolic urethane reactive diluent. The phenolic urethane reactive diluent may be made from a phenolic ester alcohol having at least one aliphatic hydroxyl group.

56 Claims, No Drawings

POLYMERIC VEHICLES WHICH INCLUDE A PHENOLIC URETHANE REACTIVE DILUENT

This application claims the benefit of U.S. Provisional Application No. 60/002,063, filed Aug. 9, 1995.

FIELD OF THE INVENTION

The present invention relates to polymeric vehicles for coating films or binders where the polymeric vehicles are thermosetting and include a phenolic urethane reactive diluent. More particularly this invention is directed to polymeric vehicles which include at least one polyol, the reactive diluent and a polyisocyanate and/or amino resin crosslinking agent.

BACKGROUND OF THE INVENTION AND DESCRIPTION OF THE PRIOR ART

One of the primary components in paint is the "film former" that provides a film for the protective function of a substrate coated with paint. Film forming components of liquid paints include resins which have required organic solvents to provide the resins with suitable viscosities such that the paint can be applied by existing commercial application equipment. Use of solvents, however, raises at least two problems. First, in the past and potentially in the future, petrochemical shortages mitigate against the use of organic solvent in great volumes. Second, environmental concern mitigates against the use of organic solvents and requires such use be minimized.

Thermosetting coating compositions, particularly coating compositions which include polyester, alkyd, acrylic and epoxy polymers are often materials of choice for making film formers for various substrates to which the coating composition is applied. Coating compositions provide a protective function for the substrate. Hence, coating compositions are generally formulated to provide a balance of properties which will maximize hardness, flexibility, solvent resistance, corrosion resistance, weatherability, acid resistance, hydrolytic stability and gloss with an emphasis on certain properties depending upon the purpose for which the coating is intended.

It has been a continuing challenge to provide coating compositions which upon thermosetting provide films with desired film properties such as hardness, flexibility, solvent resistance, corrosion resistance, weatherability, acid resistance, hydrolytic stability and gloss, reduce VOCs and still retain the ability to have the viscosities of the polymeric vehicle and formulated coating composition made therefrom such that the formulated coating composition can be applied with existing commercial application equipment.

U.S. Pat. No. 4,331,782 to Linden, U.S. Pat. Nos. 3,836,491 and 3,789,044 to Taft et al. and U.S. Pat. No. 3,409,579 to Robbins describe phenol capped polymers which are crosslinked with polyisocyanates. They do not involve the use of a phenolic urethane reactive diluent which is cross linked or the use of such a diluent in a system which includes a polyol, diluent and crosslinking agent.

OBJECTS OF THE INVENTION

It is an object of the invention to provide a coating composition which will maximize film properties such as hardness, flexibility, solvent resistance, corrosion resistance, weatherability, acid resistance, hydrolytic stability and gloss.

It is another object of the invention to provide a coating composition which will be low in VOCs.

It is an object of this invention to provide formulated compositions which are solventless as well as formulated coating compositions which are thinned by organic solvents and/or water.

Another object of this invention is to control viscosity of the polymeric vehicle through the use of a phenolic urethane reactive diluent and the ability to use commercial equipment for the application of the formulated coating composition made with the polymeric vehicle through such viscosity control.

Further objects and advantages of the invention will be found by reference to the following description.

SUMMARY OF THE INVENTION

The present invention is directed to a polymeric vehicle, a formulated coating composition, a coating binder made from the polymeric vehicle and a method for making the polymeric vehicle where the polymeric vehicle includes a phenolic urethane reactive diluent. The latter reactive diluent improves film properties such as hardness. When the components of the polymeric vehicle are at low molecular weights and when the phenolic reactive diluent is at low molecular weights such as in the range of from about 240 to about 1140, the reactive diluent hardens the coating binder often without increasing the viscosity of the polymeric vehicle and coating composition. In an important aspect, the invention provides a high solids or solventless polymeric vehicle and/or formulated coating composition where the viscosity of the blend which constitutes the polymeric vehicle (which includes the phenolic reactive diluent), will be in the range of from about 0.1 to about 20 Pa.s at about 20 to about 60° C. at a shear rate of at least about 1,000 and preferably in the range of about 1,000 to about $1 \times 10^6$ In a very important aspect, the phenolic reactive diluent has the formula

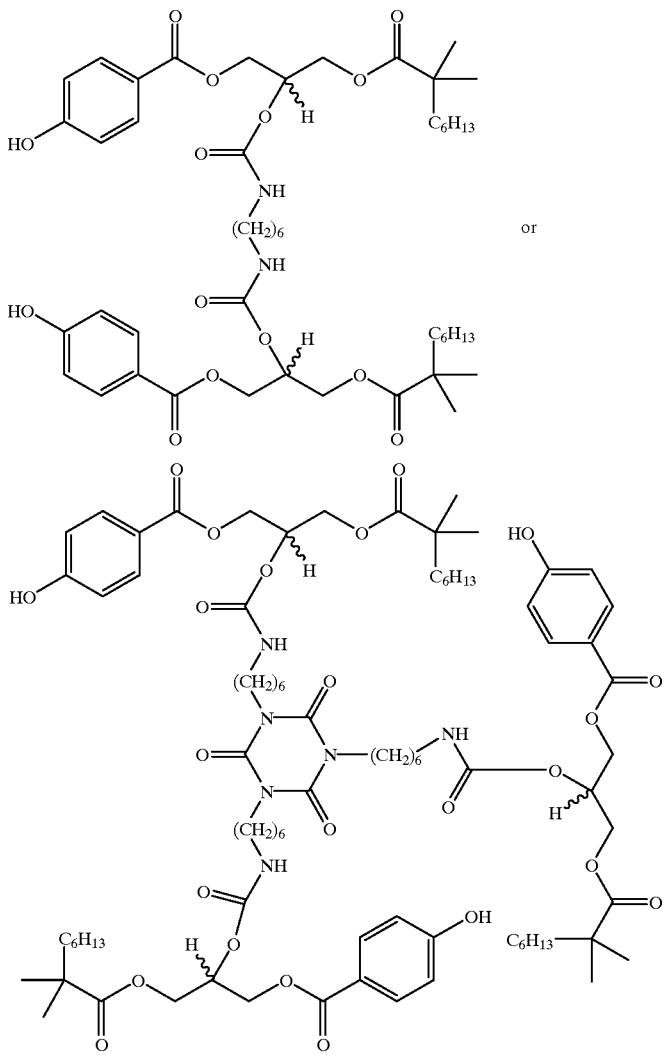

The phenolic urethane reactive diluent is the reaction product of a phenolic ester alcohol having at least one aliphatic hydroxyl group and a compound having an average isocyanate functionality of from about 1.9 to 20 isocyanate groups per molecule. The phenolic ester alcohol is the reaction product of a phenol carboxylic acid and a compound having an epoxy functionality. In one important aspect, the phenolic ester alcohol has at least two ester linkages, at least one phenolic hydroxyl group and at least one aliphatic hydroxyl group, and in a very important aspect, about one aliphatic hydroxyl group which aliphatic hydroxyl is primary or secondary. Included in this aspect, the phenolic ester alcohol has the general formula

"A"

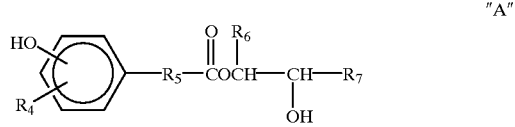

wherein $R_4$ is selected from the group consisting of hydrogen, halogen, hydroxyl, $C_1$ to $C_8$ alkyl and $C_1$ to $C_8$ alkoxy, $R_5$ is a direct bond or a $C_1$ to $C_{20}$ organic radical which may incorporate another phenol or aliphatic hydroxyl, ester, ether and/or carbonate group in its structure, $R_6$ is hydrogen or a $C_1$ to $C_{20}$ organic radical which may include one or more ester linkages or a direct bond which may form with $R_7$ part of a 5 or 6 carbon atom cyclic ring structure, $R_7$ is $CH_2R_8$ wherein $R_8$ is selected from the group consisting of hydroxy, $OR_9$, $OOCR_{10}$ and $R_{11}$ wherein $R_9$ is a primary or secondary aliphatic group containing 3 to 20 carbon atoms which may include one or more ester linkages or an aromatic group containing 6 to 20 carbon atoms, $R_{10}$ is a primary, secondary or tertiary aliphatic group containing 4 to 20 carbon atoms which may include one or more ester linkages or an aromatic group containing 6 to 20 carbon atoms, and $R_{11}$ is a $C_2$ to $C_{20}$ organic radical which may include one or more ester linkages and where the organic radical may form with $R_6$ part of a 5 or 6 carbon atom cyclic ring structure. In a particularly important aspect, $R_5$ or $R_8$ has the ester linkages or groups. As used herein, an ester group or linkage means

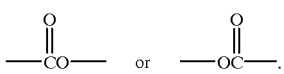

The —OH expressly shown as bonded to the —CH— group in formula A is illustrative of an aliphatic hydroxyl group.

In another important aspect of the invention, the phenolic ester alcohol is the reaction product of hydroxybenzoic acid, such as para hydroxybenzoic acid, and a monoglycidyl compound having a molecular weight in the range of from about 110 to 1000 such as the monoglycidyl compound with the formula ("B")

where R represents a mixture of aliphatic groups, most preferably the three R groups in the glycidyl compound having a total of 8 carbon atoms and which the glycidyl compound is commercially available from Exxon Chemical Company under the trademark Glydexx®.

In yet another important aspect of the invention, the polymeric vehicle comprises the phenolic urethane reactive diluent; at least one polyol having an average hydroxyl functionality of from about 1.9 to about 20 hydroxyls per molecule and a molecular weight of at least 200; and at least one crosslinker selected from the group consisting of a compound having an isocyanate functionality of from about 1.9 to about 20 isocyanate groups per molecule, an amino resin having a crosslinking functionality of from about 3 to about 30 crosslinking groups per molecule and mixtures of the isocyanate compound and amino resin.

In a very important aspect of this invention, the polymeric vehicle includes the polyol which is a polyester, alkyd or acrylic polyol, the reactive diluent made with the phenolic ester alcohol having one aliphatic hydroxyl group, where the isocyanate compound used to make the reactive diluent has an average isocyanate functionality of about 3 and an amino resin crosslinker. In the aspect of the invention which includes polyol, phenolic urethane reactive diluent and crosslinker, each is in relative amounts effective for providing an acceptable coating binder which generally will have a pencil hardness of at least about HB, an impact resistance of at least about 20-inch pounds direct and at least about 20-inch pounds reverse at a film thickness of about 0.5 mil dry.

In an important aspect, the coating binder will have a hardness of about F at a thickness of about 0.5 mil dry and an impact resistance of about 30-inch pounds direct and 30-inch pounds reverse at such thickness.

Generally the polymeric vehicle may have from about 0 to about 80 weight percent polyol, from about 10 to about 80 weight percent reactive diluent and from about 8 to about 50 weight percent crosslinker where the crosslinker is an amino resin and from about 8 to about 50 weight percent crosslinker where the crosslinker has an isocyanate functionality. Where a polyol is present in the blend of the polymeric vehicle, the polymeric vehicle generally will comprise at least about 15 weight percent polyol and preferably will have from about 15 to about 60 weight percent polyol.

DESCRIPTION OF THE PREFERRED EMBODIMENTS

"Polyester" means a polymer which has —C(=O)O— linkages in the main chain of the polymer.

"Polyisocyanate" can mean compounds with two or more isocyanate groups [—NC=O] which compounds may be biurets and isocyanurates.

"Biuret" means an isocyanate reacted with water in a ratio of three equivalents of isocyanate to one equivalent of water, such as the biuret of HDI shown below.

An "isocyanurate" is a six-membered ring having nitrogens at the 1, 3 and 5 positions and keto groups at the 2, 4 and 6 positions, the nitrogens being substituted with an isocyanate group, such as shown below in the isocyanurate of HDI.

"Crosslinking agent" means a compound having di- or polyfunctional isocyanate groups or a polyfunctional amino resin. The isocyanate compound or amino resin contains isocyanate or other crosslinking functional groups that are capable of forming covalent bonds with hydroxyl groups that are present on the polyol in the polymeric vehicle. The crosslinking agent may be a blend; hence, there may be more than one substance which forms a blend of substances which form covalent bonds with the hydroxyl groups of the polyol. Amino reins and polyisocyanates are such crosslinking agents.

"Polymeric vehicle" means polymeric and resinous components in the formulated coating, i.e., before film formation, including but not limited to the polyol and phenolic urethane reactive diluent.

"Coating binder" means the polymeric part of the film of the coating after solvent has evaporated and after crosslinking.

"Formulated coating" composition means the polymeric vehicle and optional solvents, as well as pigments, catalysts and additives which may optionally be added to impart desirable application characteristics to the formulated coating and desirable properties such as opacity and color to the film.

"VOC" means volatile organic compounds.

"Diol" is a compound, oligomer or polymer with two hydroxyl groups. "Polyol" is a compound, oligomer or polymer with two or more hydroxyl groups.

"Solvent" means an organic solvent.

"Organic solvent" means a liquid which includes but is not limited to carbon and hydrogen and has a boiling point in the range of from about 30° C. to about 300° C. at about one atmosphere pressure.

"Volatile organic compounds" are defined by the U.S. Environmental Protection Agency at 40 C.F.R. 51.000 of the Federal Regulations of the United States of America as any compound of carbon, excluding carbon monoxide, carbon dioxide, carbonic acid, metallic carbides or carbonates, and ammonium carbonate, which participates in atmospheric photochemical reactions.

This includes any such organic compound other than then following, which have been determined to have negligible photochemical reactivity: acetone; methane; ethane; methylene chloride (dichloromethane); 1,1,1-trichloroethane (methyl chloroform); 11,1-trichloro-2,2,2-trifluoroethane (CFC-113); trichlorofluoromethane (CFC-11); dichlorodifluoromethane (CFC-12); chlorodifluoromethane (CFC-22); trifluoromethane (FC-23); 1,2-dichloro-1,1,2,2-tetrafluoroethane (CFC-114); chloropentafluoroethane (CFC-115); 1,1,1-trifluoro 2,2-dichloroethane (HCFC-123); 1,1,1,2-tetrafluoroethane (HF-134a); 1,1-dichloro 1-fluoroethane (HCFC-141b); 1-chloro 1,1-difluoroethane (HCFC-142b); 2-chloro-1,1,1,2-tetrafluoroethane (HCFC-124); pentafluoroethane (HFC-125); 1,1,2,2-tetrafluoroethane (HFC-134); 1,1,1-trifluoroethane (HFC-143a); 1,1-difluoroethane (HFC-152a); and perfluorocarbon compounds which fall into these classes:

(i) Cyclic, branched, or linear, completely fluorinated alkanes;
(ii) Cyclic, branched, or linear, completely fluorinated ethers with no unsaturations;

(iii) Cyclic, branched, or linear, completely fluorinated tertiary amines with no unsaturations; and (iv) Sulfur containing perfluorocarbons with no unsaturations and with sulfur bonds only to carbon and fluorine. Water is not a VOC.

A "film" is formed by application of the formulated coating composition to a base or substrate, evaporation of solvent, if present, and crosslinking.

The invention is directed to a polymeric vehicle which comprises a phenolic reactive diluent as herein described. Generally, the polymeric vehicle also comprises a polyol and/or a crosslinker selected from the group consisting of a polyfunctional amino resin, an isocyanate compound having polyfunctional isocyanate functionality and mixtures of the polyfunctional amino resin and polyfunctional isocyanate compound. The polymeric vehicle and formulated coating compositions which include the polymeric vehicle of the invention may include organic solvents or may not require organic solvents or water to provide a formulated coating composition with a viscosity such that the formulated coating composition may be applied by existing application equipment. Alternatively, in another aspect, the polymeric vehicle and/or formulated coating composition of the invention permit the use of water for obtaining such a viscosity while reducing or mitigating VOCs. The phenolic urethane reactive diluent of the invention at low molecular weights, such as in the range of from about 240 to about 1140, improves film properties such as hardness often without increasing the viscosities of the polymeric vehicle and formulated coating composition. Further the phenolic urethane reactive diluent is compatible with and permits the use of other diphenolic hardeners to improve coating properties, but yet also permits the use of the additional hardeners in a formulated coating composition which may include solvents. By way of example, a diphenolic polyol ester reaction product of hydroquinone and parahydroxy benzoic acid has low solvent dispersibility or solubility, requires high-cure temperatures and often makes coatings intractable. The use of the phenolic urethane reactive diluent of the invention permits the use of such other diphenolic hardeners to improve hardness yet reduces the other problems attendant with the use of such hardeners. In high solids formulated coating compositions which include organic solvents (such as about 75 weight percent solids), one aspect of the invention contemplates the crosslinker, reactive diluent and polyol, if any, being in amounts effective for maintaining VOCs in the formulated coating composition (which includes the polymeric vehicle) to less than about 3.5 pounds of VOC per gallon of formulated coating composition while at least maintaining the pencil hardness of the coating binder, to at least about HB and maintaining an impact resistance of the coating binder to at least about 20-inch pounds direct and at least about 20-inch pounds indirect. Indeed in the high solids aspect of the invention, the invention is effective for providing formulated coating compositions having less than 2.5 pounds of VOC per gallon of formulated coating composition and in some cases less than 2.0 pounds of VOC per gallon of formulated coating composition.

In yet another important aspect, the invention is effective for providing solventless liquid formulated coating compositions (not more than about 3 weight percent organic solvent) where the polymeric vehicle in the formulated coating composition comprises the phenolic urethane reactive diluent at low molecular weight, a polyol having a molecular weight of at least 200, an average hydroxyl functionality of from about 1.9 to about 20 hydroxyls per molecule and a crosslinker selected from the group consisting of the polyfunctional amino resin, the compound with polyfunctional isocyanate functionality and mixtures of the polyfunctional amino resin and polyfunctional isocyanate.

The Phenolic Urethane Reactive Diluent

In one aspect, the phenolic urethane reactive diluent may be described as the reaction product of a phenolic ester alcohol having at least one aliphatic hydroxyl group and a compound having an average isocyanate functionality of at least 1.9. In this aspect, the ratio of an isocyanate to phenolic ester alcohol in the reaction mixture is in the range of from about 1 equivalent isocyanate group per equivalent of aliphatic hydroxyl phenolic ester alcohol. The isocyanate reacts with the aliphatic hydroxyl, which reaction is catalyzed by soluble tin salts such as dibutyl tin dilaurate and dibutyl tin diacetate and divalent zinc salts such as zinc diacetate.

In another aspect, the phenolic reactive diluent has the following general formula where $R_1$ through $R_{11}$ are defined above in connection with formula A and $R_{12}$ is defined as set forth below.

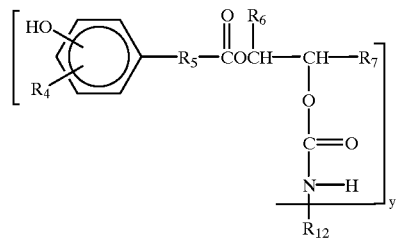

where Y=1 to 4, where $R_{12}$ is an alkyl, alkenyl, aromatic or alkyl, alkenyl and aromatic difunctional radical, where the radical can include or be

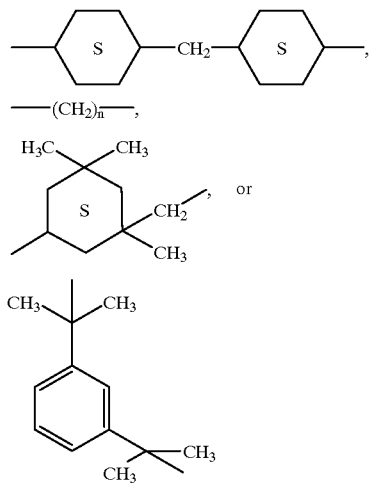

and where n=more than 1 and preferrably 6. In an important aspect of the invention, the $R_{12}$ radical is

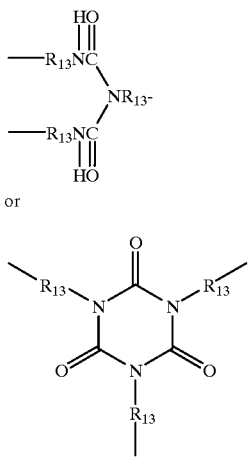

or

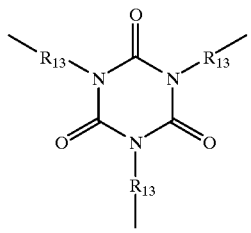

where $R_{13}$ is a difunctional radical as described above.

The phenolic ester alcohol is the reaction product of a phenol carboxylic acid and an epoxy compound. In an important aspect, the phenolic ester alcohol is represented by the general formula "A"

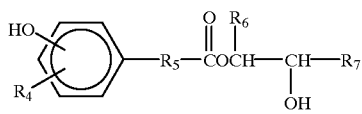

"A"

wherein $R_4$ through $R_7$ is defined above.

A phenol carboxylic acid reactant to make the phenolic ester alcohol may be used to prepare the phenolic ester reaction product of formula A. The phenol carboxylic acid has the general formula:

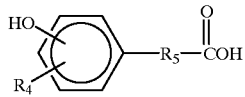

wherein $R_4$ and $R_5$ are as described above. Examples of suitable phenol carboxylic acids include hydroxybenzoic acids, acids where $R_5$ is alkylene such as phenyl acetic acid, hydroxy phenyl propionic acid, hydroxyphenyl stearic acid, and acids where in $R_5$ encompasses additional phenol functionality such as 4,4-bis hydroxyphenyl pentanoic acid and the like. In a preferred embodiment of the invention, $R_4$ in formula A is hydrogen, $R_5$ is a direct bond, $R_6$ is hydrogen and $R_7$ is $CH_2OH$, a hydrocarbon moiety or an organic moiety containing ester or ether groups and containing from 1 to about 20 carbon atoms, more preferably from about 3 to 20 carbon atoms.

In an important aspect of the invention, the phenolic ester alcohol used to make the phenolic urethane reactive diluent is the ester reaction product of a hydroxybenzoic acid and an epoxy compound. Suitable hydroxybenzoic acids include ortho-hydroxybenzoic acid (salicylic acid), meta-hydroxybenzoic acid and para-hydroxybenzoic acid (PHBA), with para-hydroxybenzoic acid being most preferred.

The epoxy compound may be selected from the group consisting of glycidyl esters, glycidyl alcohols, glycidyl ethers, linear epoxies and aromatic epoxies. These include glycidol, glycidyl ethers of the structure:

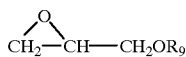

glycidyl esters of the structure:

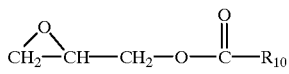

glycidyl or oxirane compounds having the structure:

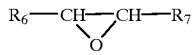

and cycloaliphatic epoxy compounds having the structures:

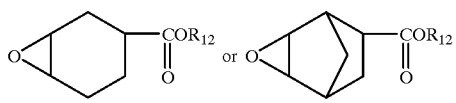

wherein $R_{12}$ is an organic radical having 1–12 carbon atoms which can include ether, ester, hydroxyl or epoxy groups, as well as other cycloaliphatic compounds having the structures:

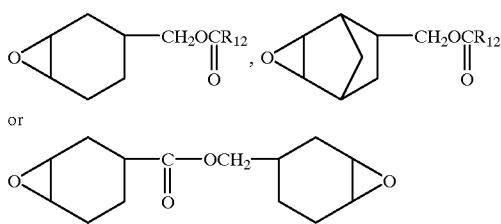

Other epoxy materials include epoxidized alpha-olefins and bis aromatic epoxies such as the reaction product of bisphenol A or F with epichlorohydrin.

Suitable epoxy compounds particularly include monoepoxides containing a terminal glycidyl group or polyepoxides containing internal oxirane or glycidyl groups or terminal glycidyl groups. Suitable epoxy compounds include glycidyl acrylate or methacrylate monomers, alkyl glycidyl ether monomers, and low molecular weight copolymers of one or more of these monomers with one or more ethylenically unsaturated monomers such as acrylates, methacrylates, vinyl aromatic monomers and the like.

Other suitable epoxy compounds include the ester reaction products of epichlorohydrin with mono- or dibasic aliphatic or aromatic carboxylic acids or anhydrides containing from about 1 to 20 carbon atoms. Inclusive of such acids are aliphatic acids such as acetic, butyric, isobutyric, lauric, stearic, maleic and myristic acids and aromatic acids such as benzoic, phthalic, isophthalic and terephthalic acids as well as the corresponding anhydrides of such acids. Preferred such acids are primary, secondary or tertiary aliphatic carboxylic acids containing from 5 to 13 carbon atoms. In a very important aspect of the invention, an epoxy compound of this type is the glycidyl ester of a mixed aliphatic, mostly tertiary, mono carboxylic acid with an average of 9 to 11 carbon atoms such as available from Exxon Chemical Co., under the trade name GLYDEXX® or from Shell Chemical Co., under the trade name CAR-DURA® E ester. These may be represented by the general formula "B". (Glydexx® general formula).

Still other epoxy compounds include glycidyl ether reaction products of epihalohydrin with aliphatic or aromatic alcohols or polyols containing from about 1 to 20 carbon atoms. Suitable alcohols include aromatic alcohols such as bisphenol, bisphenol A, bisphenol F, phenolphthalein and novolac resins; aliphatic alcohols such as ethanol, isopropanol, isobutyl alcohol, hexanol, stearyl alcohol and the like; and aliphatic polyols such as ethylene glycol, propylene glycol and butylene glycol.

Other epoxy compounds which may be used include the mono-epoxides of $C_8$ to $C_{20}$ alpha mono-olefins.

The epoxy compound may also comprise epoxidized fatty compounds. Such epoxidized fatty compounds include epoxidized fatty oils, epoxidized fatty acid esters of monohydric alcohols, epoxidized fatty acid esters of polyhydric alcohols, epoxidized fatty nitriles, epoxidized fatty amides, epoxidized fatty amines and epoxidized fatty alcohols. Suitable alicyclic epoxide and polyepoxide materials include dicyclopentadiene diepoxide, limonene diepoxide, and the like. Additional useful epoxides include for example, vinyl cyclohexane dioxide, bis(3,4-epoxycyclohexyl) adipate, 3,4-epoxycyclohexylmethyl-3,4-epoxy-cyclohexane carboxylate and 2-(3,4-epoxycyclohexyl-5,5-spiro-3,4-epoxy)cyclohexane-metadioxane.

In a very important aspect of making the phenolic ester used to make the phenolic urethane reactive diluent, the hydroxybenzoic acid/epoxy reaction product of this invention may be formed by reacting the hydroxybenzoic acid and the epoxy compound to provide a phenolic ester alcohol with one aliphatic hydroxyl group, optionally in a solvent therefor, at a temperature ranging from about 90° to about 120° C. to initiate such reaction. Once the reaction is initiated, such reaction is exothermic, and the reaction temperature can rise to a temperature of about 150° to 175° C. usually without application of external heat. The reaction temperature then is maintained at about 150° C. to 170° C. (and preferably less than about 200° C.) until the reaction has been determined to be substantially complete.

Reaction products of reduced discoloration can be produced by control of the maximum temperature of the exothermic reaction. This can be achieved by a staged and/or incremental addition of one of the reactants, e.g. the epoxy reactant, so that the reaction temperature is maintained at a temperature of about 150° C. or below. The remainder of that reactant may then be added in stages or continuously while maintaining the reaction temperature below about 150° C. This process modification gives rise to reaction products having lower Color Index values.

Approximately stoichiometric quantities of the epoxy compound and the phenol carboxylic acid are used in the reaction, although a slight molar excess of epoxy may be necessary to drive the reaction to completion.

The phenolic urethane reactive diluent is the reaction product of the phenolic ester alcohol, such as the one shown in formula A, and a composition having a polyisocyanate functionality, such as a polyisocyanate, biuret or isocyanurate. One equivalent isocyanate is reacted for every equivalent of aliphatic hydroxyl group in the phenolic ester alcohol. The reaction is catalyzed by an organo metallic catalyst such as dibutyl tin dilaurate and zinc acetate. In many instances the reaction proceeds at room temperature, and if not, the reaction mixture may be heated as is known to drive the reaction such that the aliphatic hydroxyl groups are reacted to provide the phenolic urethane reactive diluent which has free hydroxyl groups extending from the aromatic ends of the molecule. The phenolic urethane reactive diluent may be made with low molecular weight diisocyanates such as hexamethlenediisocyanate (HDI) as well as polyisocyanates which have molecular weights up to about 20,000. Unblocked or blocked di- or polyisocyanates, unblocked or blocked biurets and blocked or unblocked isocyanurates all may be reacted with the aliphatic hydroxyls of the phenolic ester to form carbamate linkages [—OC(=O)N(—H)—] and the phenolic urethane reactive diluent. This diluent serves as a hardener to harden the coating binder without increasing the viscosities of the formulated coating composition and polymeric vehicle. In many important instances, the phenolic urethane reactive diluent keeps the viscosity of the polymeric vehicle low to aid in the reduction of VOCs.

Diisocyanates which may be used in the invention additional to HDI include isophorone diisocyanate (IPDI), tetramethylxylene diisocyanate (TMXDI), and other aliphatic diisocyanates such as trimethylene diisocyanate, tetramethylene diisocyanate, pentamethylene diisocyanate, 1,2-propylene diisocyanate, 2,3-butylene diisocyanate, 1,3-butylene diisocyanate, 2,4,4- or 2,2,4-trimethylhexamethylene diisocyanate; cycloalkylene diisocyanates such as 1,3-cyclopentane-diisocyanate, 1,4-cyclohexane-diisocyanate and 1,3-cyclohexane-diisocyanate; and aromatic diisocyanates such as m-phenylene diisocyanate, p-phenylene diisocyanate, 4,4'-diphenyldiisocyanate, 1,5-naphthalene diisocyanate, 4,4'-diphenylmethane diisocyanate, 2,4- or 2,6-tolulene diisocyanate.

The polyisocyanates may be dimerized or trimerized diisocyanates such as trimerized HDI or IPDI and triisocyanates such as triphenylmethane-4,4', 4"-triisocyanate, 1,3,5-triisocyanatobenzene, 1,3,5-triisocyanatocyclohexane, 2,4,6-triisocyanatotoluene and ω-isocyanatoethyl-2,6-diisocyanatocaproate; and tetraisocyanates, such as 4,4'-diphenyldimethylmethane-2,2', 5,5'-tetraisocyanate.

They also may be polymers or copolymers with vinyl monomers of isocyanate functional monomers such as

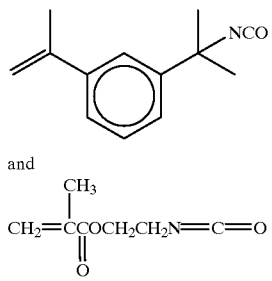

and $CH_2{=}\overset{CH_3}{\underset{}{C}}\underset{\overset{\|}{O}}{C}OCH_2CH_2N{=}C{=}O$ In another aspect of the invention, unblocked or blocked biurets such as the biuret of hexamethylene diisocyanate (HDI) which biuret has the structure

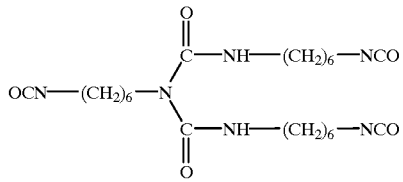

and is a trimerized product of hexamethylene diisocyanate and water may be used in lieu of polyisocyanates.

In a particularly important aspect of the invention an isocyanate, biuret, isocyanurate or blends thereof with an —NC=O functionality of about 3 provides a particularly useful phenolic urethane reactive diluent when reacted with a phenolic ester alcohol which is a reaction product of a hydroxybenzoic acid such as PHBA and glycidyl ester of a mixed aliphatic such as Glydexx®.

Agents which block the isocyanate groups and "deblock" at elevated temperature are known and are used in the invention. These include oximes, lactams, imines, carbamates such as acetone oxime, methyl ethyl ketoxime, ε-caprolactam and ethyleneimine.

The Crosslinking Agent

The crosslinking agent which is used with the reactive diluent may be one or more unblocked or blocked polyisocyanates, one or more unblocked or blocked biurets, one or more blocked or unblocked isocyanurates, one or more amino resins and/or a blend of crosslinkers at least one crosslinker in the blend having the —NC=O functionality and one crosslinker in the blend being an amino resin crosslinker. Effective amounts of crosslinker for permitting the polymeric vehicle to crosslink into a coating binder with the hardness and impact resistance as described above are used. When the polymeric vehicle includes a polyol and reactive diluent, the polymeric vehicle generally comprises at least about 15 weight percent polyol and generally from about 15 to about 60 weight percent polyol, from about 10 to about 80 weight percent reactive diluent and from about 8 to about 50 weight percent crosslinker where the crosslinker is an amino resin and from about 8 to about 50 weight percent crosslinker where the crosslinker has an isocyanate functionality.

The same polyisocyanates, biurets and isocyanurates may be used as crosslinkers that are used to make the phenolic urethane reactive diluent. If, however, a compound which is high in isocyanate functionality (numerous isocyanate groups) is used to make the reactive diluent, then a compound which is lower in isocyanate functionality should be used as a crosslinker.

Methylol (alkoxymethyl) amino crosslinking agents are suitable for use in the present invention and are well known commercial products, and are generally made by the reaction of di (poly) amide (amine) compounds with formaldehyde and, optionally, a lower alcohol.

Examples of suitable amino-crosslinking resins include one or a mixture of the following materials:

Melamine Based Resins

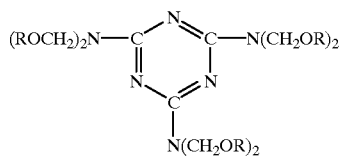

wherein R is the following:

R=CH₃ (Cymel)® 300, 301, 303);
R=CH₃, C₂H₅ (Cymel® 1116);
R=CH₃, C₄H₉ (Cymel® 1130, 1133);
R=C₄H₉ (Cymel® 1156); or
R=CH₃, H (Cymel® 370, 373, 380, 385).

The preferred melamine is hexamethoxymethyl melamine.

Benzoquanamine Based Resins

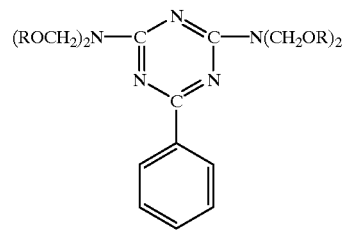

wherein

R=CH₃, C₂H₅ (Cymel® 1123).

Urea Based Resins

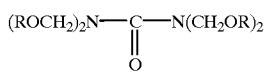

wherein:

R=CH₃, H (Beetle™ 60, Beetle™ 65); or
R=C₄H₉ (Beetle™ 80).

Gycoluryl Based Resins

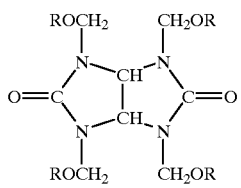

wherein:

R=CH₃, C₂H₅ (Cymel® 1171); or
R=C₄H₉ (Cymel® 1170).

The Polyols in the Polymeric Vehicle

The polyols which are used in the invention are selected from the group consisting of polyesters, alkyd polymers, acrylic polymers and epoxy polymers. The polyols have an number average molecular weight ($M_n$) of at least about 200, and may generally range from about 200 up to about 20,000, more preferably from about 280 up to about 10,000, and most preferably from about 300 up to about 3,000 to 6,000. Glass transition temperatures (Tg) of these materials may generally range from as low as −90° C. up to +100° C. or higher.

The diesters and polyesters may be prepared by well known condensation processes using a molar excess of diol. Preferably the molar ratio of diol to dicarboxylic acid is p+1:p wherein p represents the number of moles of dicarboxylic acid. The reaction may be conducted in the absence of or presence of a suitable polycondensation catalyst as is known in the art.

Polyesters also can be made from carboxylic acids and oxiranes, such as

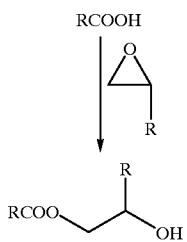

R=H, alkyl, aryl

Some preferred examples of the diols used to make the polyester polyols are one or more of the following: neopentyl glycol; ethylene glycol; hexamethylenediol; 1,2-cyclohexanedimethanol; 1,3-cyclohexanedimethanol; 1,4-cyclohexanedimethanol; diethylene glycol; triethylene glycol; tetraethylene glycol; dipropylene glycol; polypropylene glycol; hexylene glycol; 2-methyl-2-ethyl-1,3-propanediol; 2-ethyl-1,3-hexandediol; 1,5-pentanediol; thiodiglycol; 1,3-propanediol; 1,2-propanediol; 1,2-butanediol; 1,3-butanediol; 2,3-butanediol; 1,4-butanediol; 2,2,4-trimethyl-1,3-pentanediol; 1,2-cyclohexanediol; 1,3-cyclohexanediol; 1,4-cyclohexanediol; neopentyl diol hydroxy methyl isobutyrate, and mixtures thereof. Examples of polyols include triols such as glycerine, timethylol ethane, trimethylol propane, pentaerythritol and the like.

The diols are reacted with carboxyl groups to make the polyesters. The carboxyl groups may be present in the form of anhydride groups, lactone groups, or equivalent ester forming derivatives such as the acid halide or methyl ester. The dicarboxylic acids or derivatives are preferably one or more of the following: phthalic anhydride, terephthalic acid, isophthalic acid, naphthalene dicarboxylic acids, adipic acid, succinic acid, glutaric acid, fumaric acid, maleic acid, cyclohexane dicarboxylic acid, azeleic acid, sebasic acid, dimer acid, caprolactone, propiolactone, pyromellitic dianhydride, substituted maleic and fumaric acids such as citraconic, chloromaleic, mesaconic, and substituted succinic acids such as aconitic and itaconic, and mixtures thereof. Many commercially available polyesters are produced using a combination of aromatic and aliphatic dicarboxylic acids or a combination of cycloaliphatic and aliphatic dicarboxylic acids or combinations of all three types. However, where polyesters having low viscosity and low solvent content are desired, the most preferred acids used for the purposes of this invention are linear saturated or unsaturated aliphatic dicarboxylic acids having from 2 to 10 carbon atoms such as succinic, glutaric, adipic, and similar materials.

The acrylic polymers which may be used as the polyol component in the present invention are acrylic copolymer resins. The acrylic copolymer resin is prepared from at least one hydroxy-substituted alkyl (meth) acrylate and at least one non-hydroxy-substituted alkyl (meth) acrylate. The hydroxy-substituted alkyl (meth) acrylates which can be employed as monomers comprise members selected from the group consisting of the following esters of acrylic or methacrylic acid and aliphatic glycols: 2-hydroxyethyl acrylate, 3-chloro-2-hydroxypropyl acrylate; 1-hydroxy-2-acryloxy propane; 2-hydroxypropyl acrylate; 3-hydroxypropylacrylate; 2,3-dihydroxypropylacrylate; 3-hydroxybutyl acrylate; 2-hydroxybutyl acrylate; 4-hydroxybutyl acrylate; diethyleneglycol acrylate; 5-hydroxypentyl acrylate; 6-hydroxyhexyl acrylate; triethyleneglycol acrylate; 7-hydroxyheptyl acrylate; 1-hydroxy-2-methacryloxy propane; 2-hydroxypropyl methacrylate; 2,2-dihydroxypropyl methacrylate; 2-hydroxybutyl methacrylate; 3-hydroxybutyl methacrylate; 2-hydroxyethyl methacrylate; 4-hydroxybutylmethacrylate; 3,4-dihydroxybutyl methacrylate; 5-hydroxypentyl methacrylate; and 7-hydroxyheptyl methacrylate. The preferred hydroxy functional monomers for use in preparing the acrylic resins are hydroxy-substituted alkyl (meth) acrylates having a total of 5 to 7 carbon atoms, i.e., esters of $C_2$ to $C_3$ dihydric alcohols and acrylic or methacrylic acids. Illustrative of particularly suitable hydroxy-substituted alkyl (meth) acrylate monomers are 2-hydroxyethyl methacrylate, 2-hydroxyethyl acrylate, 2-hydroxybutyl acrylate, 2-hydroxypropyl methacrylate, and 2-hydroxypropyl acrylate.

Among the non-hydroxy-substituted alkyl (meth) acrylate monomers which may be employed are alkyl (meth) acrylates. Preferred nonhydroxy unsaturated monomers are esters of $C_1$ to $C_{12}$ monohydric alcohols and acrylic or methacrylic acids, e.g., methyl methacrylate, hexyl acrylate, 2-ethylhexyl acrylate, lauryl methacrylate, glycidyl methacrylate, etc. Examples of particularly suitable monomers are butyl acrylate, butyl methacrylate and methyl methacrylate.

Additionally, the acrylic copolymer polyol resins used in the present invention may include in their composition other monomers such as acrylic acid and methacrylic acid, monovinyl aromatic hydrocarbons containing from 8 to 12 carbon atoms (including styrene, alpha-methyl styrene, vinyl toluene, t-butyl styrene, chlorostyrene and the like), vinyl chloride, vinylidene chloride, acrylonitrile, epoxy-modified acrylics and methacrylonitrile.

The acrylic copolymer polyol preferably has a number average molecular weight not greater than about 30,000, more preferably between about 280 and about 15,000, and most preferably between about 300 and about 5000.

Alkyd polymers may be used as the polyol component of this invention. These alkyd resins have a number average molecular weight in the range of from about 500 to about 20,000, are oil modified polyester resins and are broadly the product of the reaction of a dihydric alcohol and a dicarboxylic acid or acid derivative and an oil, fat or carboxylic acid derived from such oil or fat which acts as a modifier. Such modifiers are drying oils, semi-drying oils or non-drying oils. The polyhydric alcohol employed is suitably an aliphatic alcohol, and mixtures of the alcohols also may be employed. The dicarboxylic acid, or corresponding anhydrides, may be selected from a variety of aliphatic carboxylic acids or mixtures of aliphatic and aromatic dicarboxylic acids. Suitable acids and acid anhydrides include, by way of example, succinic acid, adipic acid, phthalic anhydride, isophthalic acid, trimellitic acid (anhydride) and bis 3,3', 4,4'-benzophenone tetracar-boxylic anhydride. Mixtures of these acids and anhydrides may be employed to produce a balance of properties. As the drying oil or fatty acid there is suitably employed a saturated or unsaturated fatty acid of 12 to 22 carbon atoms or a corresponding triglyceride, that is, a corresponding fat or oil, such as those contained in animal or vegetable fats or oils. Suitable fats and oils include tall oil, castor oil, coconut oil, lard, linseed oil, palm oil, peanut oil, rapeseed oil, soybean oil and beef tallow. Such fats and oils comprise mixed triglycerides of such fatty acids as caprylic, capric, lauric, myristic, palmitic, and stearic and such unsaturated fatty acids as oleic, eracic, ricinoleic, linoleic and linolenic. Chemically, these fats and oils are usually mixtures of two or more members of the class. Alkyd resins made with saturated monocarboxylic acids and fats are preferable where improved weather resistance is of prime concern.

Epoxy polymers having a number average molecular weight in the range of from about 500 to about 6,000 may be used as the polyol component of this invention.

A well known epoxy resin which may be used in the invention is made by condensing epichlorohydrin with bisphenol A, diphenylol propane. An excess of epichlorohydrin is used, to leave epoxy groups on each end of the low-molecular weight polymer:

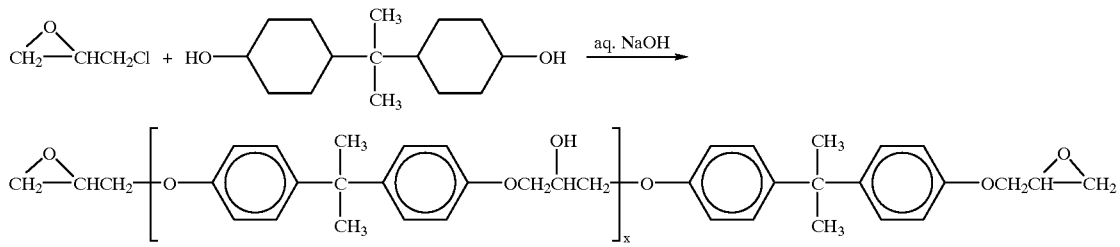

The viscosity of the polymer is a function of molecular weight, the higher the molecular weight the more viscous the polymer.

Other hydroxyl-containing compounds, including resorcinol, hydroquinone, glycols, and glycerol may be used in lieu of bisphenol A.

Solvents and Optional Ingredients in the Polymeric Vehicle

There are different aspects of the invention which include a polymeric vehicle effective for providing a formulated coating composition which is without any added organic solvent or at least does not have more than about 3 weight percent organic solvent, a polymeric vehicle which is effective for providing a high solids, low VOC formulated coating composition and a water-thinned formulated coating composition. Suitable optional solvents which may be included in the curable compositions of the invention comprise toluene, xylene, ethylbenzene, tetralin, naphthalene, and solvents which are narrow cut aromatic solvents comprising $C_8$ to $C_{13}$ aromatics such as those marketed by Exxon Chemical Company under the name Aromatic 100, Aromatic 150, and Aromatic 200.

Other suitable solvents include acetone, methyl ethyl ketone, methyl isobutyl ketone, methyl amyl ketone, methyl isoamyl ketone, methyl heptyl ketone, isophorone, isopropanol, n-butanol, sec.-butanol, isobutanol, amyl alcohol, isoamyl alcohol, hexanols, and heptanols.

Suitable oxygenerated solvents include propylene glycol monomethyl ether acetate, propylene glycol propyl ether acetate, ethyl ethoxypropionate, dipropylene glycol monomethyl ether acetate, propylene glycol monomethyl ether, and like materials. Other such solvents include alkyl esters such as ethyl acetate, n-propyl acetate, butyl acetate, amyl acetate, mixtures of hexyl acetates such as sold by Exxon Chemical Company under the name EXXATE® 600 and mixtures of heptyl acetates sold under the name EXXATE® 700. The list should not be considered as limiting, but rather as examples of solvents which are useful in the present invention. The type and concentration of solvents are generally selected to obtain formulation viscosities and evaporation rates suitable for the application and baking of the coatings.

Suitable pigments which may be included in the compositions of this invention are those opacifying pigments normally used in paint and coating formulations and include titanium dioxide, zirconium oxide, zircon, zinc oxide, iron oxides, antimony oxide, carbon black, as well as chrome yellows, greens, oranges, mixed metal oxides, ceramic pigments and the like. Preferred pigments include rutile $TiO_2$ and particularly weather-resistant coated types of $TiO_2$. The pigments may also be blended with a suitable extender material which does not contribute significantly to hiding power. Suitable extenders include silica, barytes, calcium sulfate, magnesium silicate (talc), aluminum oxide, aluminum hydroxide, aluminum silicate, calcium silicate, calcium carbonate (mica), potassium aluminum silicate and other clays or clay-like materials.

Satisfactory baking schedules for formulations of the present invention vary widely including, but not limited to, low temperature bakes of about 20 to 30 minutes at temperatures between 90° C. and 105° C. for large equipment applications and high temperature bakes of about 5 to 10 seconds in 300° C. to 375° C. air for coil coating applications. In general, the substrate and coating should be baked at a sufficiently high temperature for a sufficiently long time so that essentially all solvents are evaporated from the film and chemical reactions between the polymer and the crosslinking agent proceed to the desired degree of completion. The desired degree of completion also varies widely and depends on the particular combination of cured film properties required for a given application. Further, catalyzed crosslinking also may be effected at ambient temperatures using many isocyanate-type crosslinkers.

Acid catalysts may be used to cure systems containing hexamethoxymethyl melamine and other amino crosslinking agents, and a variety of suitable acid catalysts are known to one skilled in the art for this purpose. These include, for example, p-toluene sulfonic acid, methane sulfonic acid, nonylbenzene sulfonic acid, dinonylnapthalene disulfonic acid, dodecylbenzene sulfonic acid, phosphoric acid, phosphorous acid, phenyl acid phosphate, butyl phosphate, butyl maleate, and the like or a compatible mixture of them. These acid catalysts may be used in their neat, unblocked form or combined with suitable blocking agents such as amines. Typical examples of unblocked catalysts are the King Industries, Inc., products with the tradename K-CURE®. Examples of blocked catalysts are the King Industries, Inc., products with the tradename NACURE®.

Catalysts for isocyanates include soluble tin salts such as dibutyltin dilaurate and dibutyltin diacetate, divalent zinc salts such as zinc diacetate, and tertiary bases including tertiary amines, such as diazabicyclooctane.

The amount of catalyst employed typically varies inversely with the severity of the baking schedule. In particular, smaller concentrations of catalysts are usually required for higher baking temperatures or longer baking times. Typical catalyst concentrations for moderate baking conditions (15 to 30 minutes at 150° C.) would be about 0.2 to 0.5 wt % catalyst solids per polymer plus crosslinking agent solids. Higher concentrations of catalyst up to about 2 wt % may be employed for cures at lower temperature or shorter times. Formulations containing sufficient residual esterification catalyst, such as phosphorous acid, may not require the inclusion of any additional crosslinking catalyst to effect a proper cure at lower curing temperatures.

tion mixture using rotary evaporation under aspirator pressure to give a sticky, resinous material which was further dried at room temperature overnight in a stream of air. The reaction is shown below.

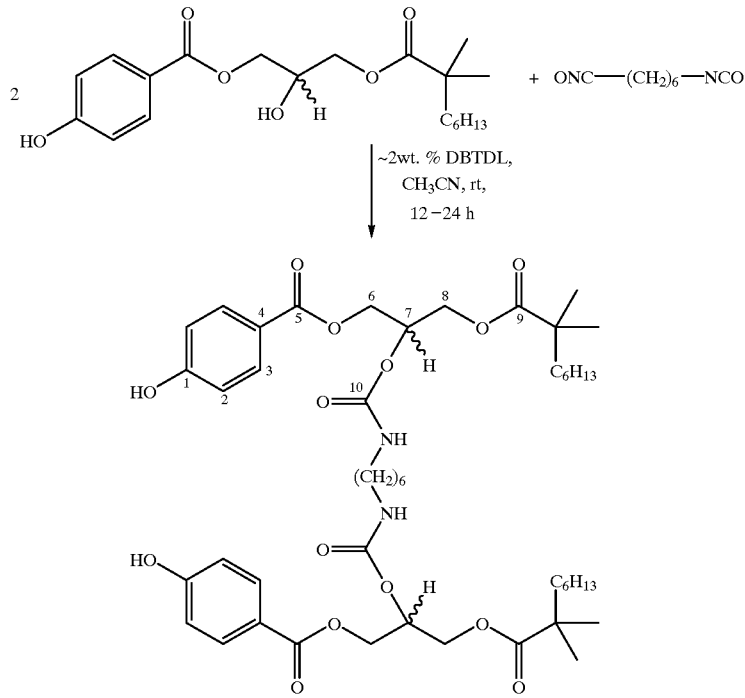

The following examples set forth compositions according to the invention and how to practice the invention.

EXAMPLE I a. Synthesis of the Phenolic Ester from a Glycidyl Ester and PHBA

Into a 1 liter flask equipped with agitation, nitrogen, heating and temperature probe, 326.6 g Glydexx® N-10 glycidyl ester and 173.4 g parahydroxy benzoic (PHBA) were charged. The mixture was heated at 110° C. At that point, an exothermic reaction takes place. The maximum temperature reached was 160° C. The solution was then cooled and discharged. Physical properties are given below.

Acid Number: 0 mg KOH/gram
NVM: >99%
Color: <3 Gardner b. Synthesis of a Phenolic Urethane Reactive Diluent by the Reaction of the Phenolic Ester with HDI (in the Molar Ratio 2:1)

Into a 25 mL round-bottomed flask equipped with a magnetic stirrer was added the phenolic ester of Example I-a (1.90 g, 5.21 mmol, MW 365) dissolved in 5 mL acetonitrile. A solution of HDI (0.44 g, 2.62 mmol, MW 168) in 5 mL acetonitrile was also added followed by dibutyltin dilaurate (DBTDL, 0.06 g, 2.5 wt % total) as catalyst. The clear, transparent solution was stirred at room temperature for 24 hours. The reaction mixture remained clear and transparent. An infrared spectrum of the reaction mixture showed a weak to no $v_{NCO}$ band. Acetonitrile was removed from the reac- Approximately 0.08 g of this sample was dissolved in 1 mL CDCl3 for NMR analysis. $^{13}C$ NMR assignments of the product are listed in the following table. It may be noticed that the chemical shift of carbon (7) substituted with the secondary —OH group changed from 72.26 ppm to 69.69 ppm. The chemical shifts of the two methylene carbons (6 and 8) appeared in the product compared to that in the phenolic ester. There are also slight changes in the chemical shifts of the ester carbons (5 and 9). The urethane carbon (10) appeared at 156.24 ppm. There was no significant chemical shifts for the phenolic carbons suggesting that no reaction took place at the phenol moiety.

| $^{13}C$ | 1 | 2 | 3 | 4 | 5 |
|---|---|---|---|---|---|
| ppm | 161.42 | 115.40 | 131.99 | 121.06 | 166.13 |
| $^{13}C$ | 6 | 7 | 8 | 9 | 10 |
| ppm | 63.21 | 69.24 | 62.69 | 176.96 | 156.24 | c. Synthesis of a Phenolic Urethane Reactive Diluent by the Reaction of the Phenolic Ester with the Isocyanurate of HDI Into a 25 mL round-bottomed flask equipped with a magnetic stirrer was added a solution of the phenolic ester of Example I-a (2.01 g, 5.51 mmol, MW 365) in 5 mL acetonitrile. A solution of the isocyanurate of HDI (Desmodur N3300, 0.96 g, 1.64 mmol, MW 585) in 5 mL acetonitrile was added to the reaction flask followed by dibutyltin dilaurate (DBTDL, 0.06 g, 2 wt. % total) as catalyst. The reaction mixture was stirred at room temperature for 24 hours. An oily, transparent product was precipitated at the bottom of the flask. Acetonitrile was removed from the reaction mixture in vacuum using a rotary evaporator under aspirator pressure. The product obtained was left overnight in a stream of air to remove the remaining solvent. Approximately 0.08 g of reactive diluent (PETG1-N3300) was dissolved in 1 mL CDCl$_3$ for NMR studies.

| $^{13}$C | 1 | 2 | 3 | 4 | 5 |
|---|---|---|---|---|---|
| ppm | 161.48 | 115.36 | 131.96 | 121.05 | 166.05 |

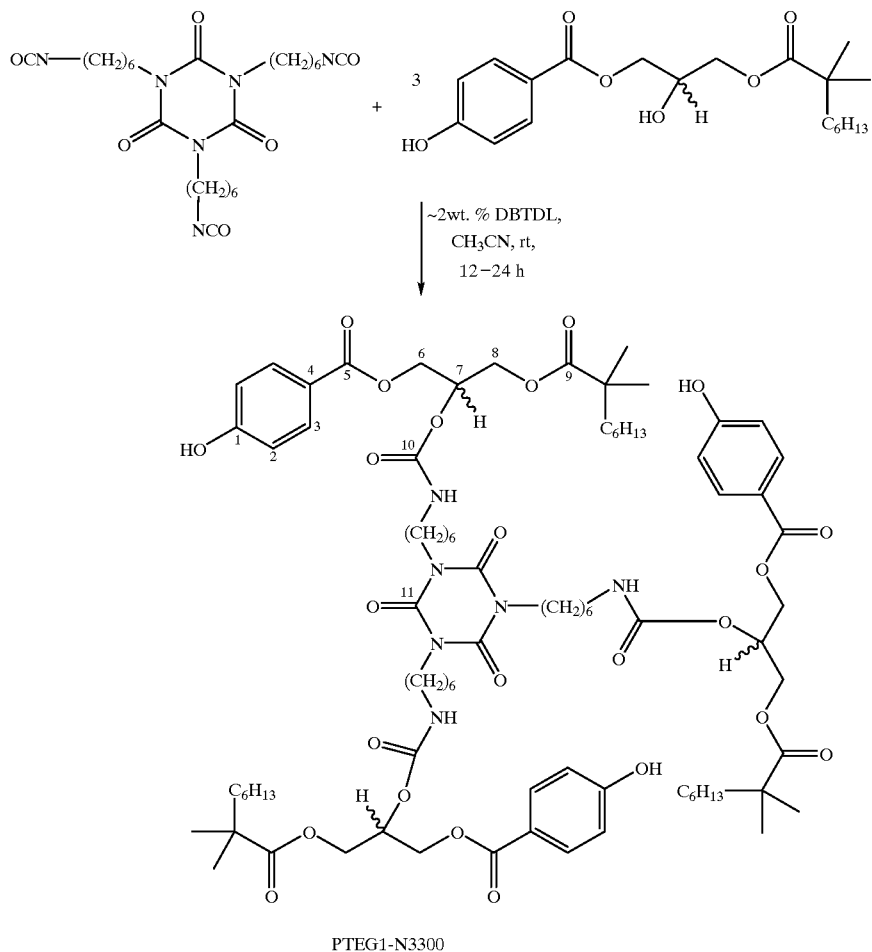

PTEG1-N3300

The $^{13}$C NMR chemical shift data are listed below. Comparing these chemical shifts with the chemical shifts of the reaction products of HDI with the phenolic ester discussed above, it may be assumed that the phenyl moiety did not undergo any reaction. The significant changes in the chemical shifts of carbons 6, 7 and 8 suggest that the secondary aliphatic —OH group reacted with the isocyanate functionality.

-continued

| $^{13}$C | 6 | 7 | 8 | 9 | 10 | 11 |
|---|---|---|---|---|---|---|
| ppm | 62.68 | 69.28 | 62.67 | 176.86 | 156.15 | 149.0 |

EXAMPLE II
Procedure for the Synthesis of Oligoesterdiol from DBE-3, DBE-5 and 1,4-Butanediol

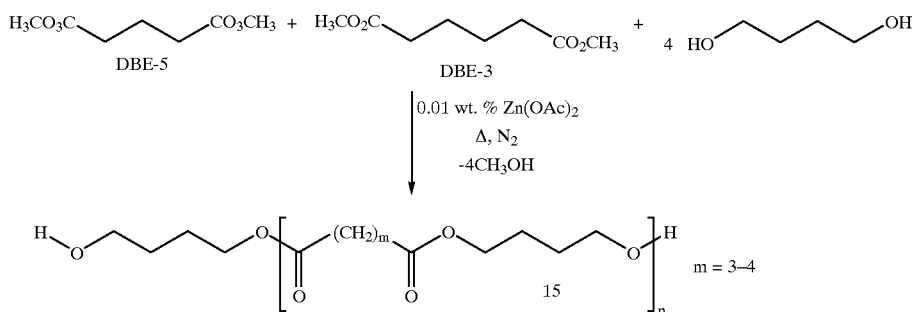

Into a 2000-mL 4-necked reaction kettle equipped with a Dean-Stark condenser, a reflux condenser, a nitrogen inlet, a thermometer inlet and a motor driven stirrer, was added 432.5 g of DBE-3 (dimethyl adipate, 2.5 mol, MW 173), 400 g of DBE-5 (dimethyl glutarate, 2.5 mol, MW 160), 924.60 g of 1,4-butanediol (10.26 mol, MW 90.12) and 0.18 g zinc acetate (0.01% of total weight). The reaction vessel was purged with nitrogen for 30 minutes. The contents of the reaction vessel were heated to 140° C. for 12 hours, 160° C. for 8 hours, 200° C. for 2 hours and 225° C. for 1 hour. The color of the reaction mixture turned light yellow upon heating to 180° C. About 390 mL of methanol distilled out of the reaction mixture during this heating process (theoretical amount of methanol to be distilled out=400 mL). The remaining methanol is assumed to have escaped. The reaction temperature was raised to 240° C. to distill the excess 1,4-butanediol. Meanwhile, Brookfield viscosity of the aliquots of the reaction mixture were performed at regular intervals of 10 minutes at 25° C. using spindle #31 at 6 rpm. In the meantime, nearly 20 mL of 1,4-butanediol was distilled out. Once the viscosity reached about 500–600 mPa.s, the reaction mixture was cooled to room temperature.

EXAMPLE III
Formulations Using the Reactive Diluent of I-c, the Diol of Example II and Cymel 300 a. Ingredients and Tests

BYK®301 & 302—Flow control agent from Byk-Chemie.
Desmodur N3300—From Miles Corporation is a cyclotrimer of 1,6-hexamethylene diisocyanate (isocyanurate of 1,6-hexamethylene diisocyanate, HDI). Its viscosity is 1.8–4 mPa.s at 25° C., and its equivalent weight is 194.
DNNDSA—Catalyst Dinonyl naphthalene disulfonic acid in isobutanol is obtained from King Industries ("Nacure-155").
GLYDEXX® N-10—Glycidal ester of a mixture of tertiary aliphatic acids having 9–11 carbon atoms available from Exxon Chemical Company.
GLYDEXX®ND-101—Same as N-10, but less pure.
SK 101—A diphenolic polyol ester which is the reaction product of hydroquinone and parahydroxy benzoic acid.

Films were prepared by casting the blended solution on panel by a 26# wire-wound draw bar.

Pencil hardness was measured according to ASTM D3364-74 standard test method for film hardness by pencil test. Impact resistance, either direct or reverse impact, was measured according to the ASTM D2794-84 standard test method for resistance of organic coatings to the effects of rapid deformation (Impact). Resistance to methyl-ethyl-ketone (MEK) was measured by double rubbing with MEK saturated nonwoven paper ("Kim-Wipe"). The nonwoven paper was kept saturated by MEK during the measurement. Dry film thickness was measured by an Elcometer Model 300 thickness gauge. Adhesion was measured according to ASTM standard (Designation: D3359-87, test method B-cross-cut tape test). VOC and NVW were measured according to ASTM standard test method for volatile content of coatings (Designation D2369-87). Viscosity was measured on a Brookfield viscometer at 6 rpm except as noted.

b. Preparation and Evaluation of Films

Polymeric vehicles and coating binders were made with the phenolic urethane reactive diluent of Example I-d and the oligoester diol of Example II.

TABLE A

| | |
|---|---|
| Oligoesterdiol* | 1.02 g |
| PTEGJ-N3300 | 0.56 g |
| Cymel 300 | 0.51 g |
| BYK-302 | 0.04 g |
| DNNDSA | 0.02 g |
| Baking Conditions | 300° F./30 min. |
| Appearance | Clear, glossy |
| Film Thickness | 1.0–1.2 mil |
| Adhesion | 3B |
| Pencil Hardness** | HB |
| MEK rub resistance | >200 |
| Impact resistance-Direct | 80 |
| Impact resistance-Reverse | 40 |

*Oligoesterdiol was synthesized from DBE-3, DBE-5 and 1,4-butanediol as per Example II.
**In the instances where the hardness was only HB, it is believed an insufficient crosslinker was used.

TABLE B

| | |
|---|---|
| Oligoesterdiol* | 0.51 g |
| PTEG1-N3300 | 0.50 g |
| Cymel 300 | 0.75 g |
| BYK-302 | 0.04 g |
| DNNDSA | 0.02 g |
| Baking Conditions | 300° F./30 min. |
| Appearance | Clear, glossy |
| Film Thickness | 0.9–1.1 mil |
| Adhesion | 4B |
| Pencil Hardness | 2H |
| MEK rub resistance | >200 |
| Impact resistance-Direct | 100 |
| Impact resistance-Reverse | 60 |

*Oligoesterdiol was synthesized from DBE-3, DBE-5 and 1,4-butanediol as per Example II.

TABLE C

| | |
|---|---|
| Oligoesterdiol* | 1.03 g |
| PTEG1-N3300 | 0.51 g |
| Cymel 300 | 1.04 g |
| BYK-302 | 0.04 g |
| DNNDSA | 0.02 g |
| Baking Conditions | 300° F./30 min. |
| Appearance | Clear, glossy |
| Film Thickness | 1.0 mil |
| Adhesion | 4B |
| Pencil Hardness | H |
| MEK rub resistance | >200 |
| Impact resistance-Direct | 80 |
| Impact resistance-Reverse | 40 |

*Oligoesterdiol was synthesized from DBE-3, DBE-5 and 1,4-butanediol.

TABLE D

| | |
|---|---|
| Oligoesterdiol* | 1.0 g |
| PTEG1-N3300 | 1.5 g |
| Cymel 300 | 1.5 g |
| BYK-302 | 0.04 g |
| DNNDSA | 0.02 g |
| Baking Conditions | 300° F./30 min. |
| Appearance | Clear, glossy |
| Film Thickness | 1.0 mil |
| Adhesion | 4B |
| Pencil Hardness | H |
| MEK rub resistance | >200 |
| Impact resistance-Direct | 160 |
| Impact resistance-Reverse | 160 |

*Oligoesterdiol was synthesized from DBE-3, DBE-5 and 1,4-butanediol as per Example II.

TABLE E

| | |
|---|---|
| Oligoesterdiol* | 1.0 g (4.219 meq) |
| PTEG1-N3300 | 1.0 g (1.786 meq) |
| Desmodur N3300 | 1.27 g |
| BYK-302 | 0.04 g |
| Baking Conditions | 300° F./30 min. |
| Appearance | Clear, glossy |
| Film Thickness | 0.9–1.0 mil |
| Adhesion | 4B |
| Pencil Hardness | HB |
| MEK rub resistance | >200 |
| Impact resistance-Direct | 160 |
| Impact resistance-Reverse | 160 |

*Oligoesterdiol was synthesized from DBE-3, DBE-5 and 1,4-butanediol as per Example II.

TABLE F

| | |
|---|---|
| Oligoesterdiol* | 1.0 g (4.219 meq) |
| PTEG1-N3300 | 1.0 g (5.48 meq) |
| Desmodur N3300 | 2.04 g |
| BYK-302 | 0.06 g |
| Baking Conditions | 300° F./30 min. |
| NVW | 98.11% |
| Appearance | Clear, glossy |
| Film Thickness | 0.9–1.0 mil |
| Adhesion | 4B–5B |
| Pencil Hardness | HB |
| MEK rub resistance | >200 |
| Impact resistance-Direct | 160 |
| Impact resistance-Reverse | 160 |

*Oligoesterdiol was synthesized from DBE-3, DBE-5 and 1,4-butanediol as per Example II.

EXAMPLE IV

Phenolic Ester Alcohol of Example I-b Reacted with HDI

In a 250-mL three-necked flat bottomed flask equipped with magnetic stirrer, condenser, thermometer and nitrogen inlet, were placed HDI (1.68 g, 0.01 mol), and a solution of the phenolic ester alcohol from Example I (AY-3 in Table) (8.75 g, 0.025 mol) dissolved in 50 mL $CH_3CN$ by heating to 70° C. Another 100 mL $CH_3CN$ was added to the reaction mixture along with dibutyltin diacetate (0.05 g, 0.5% of total reactant weight). The stirred mixture was heated on a stirrer-hotplate. The reaction mixture was refluxed for 5 hours (83° C.) and cooled to room temperature when FTIR showed absence of N=C=O peak at 2300 $cm^{-1}$. The contents of the reaction mixture were transferred into a one-necked round-bottomed flask and the solvent was removed using rotary evaporation under aspirator pressure. The product obtained was light brown viscous liquid. This aforedescribed procedure also was used in making a series of diluents which included SK101 and the isocyanate Desmodur N3300.

The formulation using Hardener C-1, etc., 1,4-BD oligoester-diol and melamine, and the properties of films made therefrom are shown in Table 1. C-1 is the same composition as C-2, but without SK101.

| AY-3 and SK101 blocked HDI | | |
|---|---|---|
| | Hardener C-2 | Hardener C-3 |
| HDI content | 1.68 g, 0.01 mol | 1.68 g, 0.01 mol |
| AY-3: SK101 | 9:1 | 8:2 |
| AY-3 content | 6.3 g, 0.018 mol | 5.6 g, 0.016 mol |
| SK101 content | 0.46 g, 0.002 mol | 0.92 g, 0.004 mol |
| dibutyltin diacetate | 0.5%, 0.04 g | 0.5%, 0.04 g |
| | Hardener C-4 | Hardener C-5 |
| HDI content | 1.68 g, 0.01 mol | 1.68 g, 0.01 mol |
| AY-3; SK101 | 7:3 | 6:4 |
| AY-3 content | 4.9 g, 0.014 mol | 4.2 g, 0.012 mol |
| SK101 content | 0.92 g, 0.004 mol | 1.84 g, 0.008 mol |
| dibutyltin diacetate | 0.5%, 0.04 g | 0.5%, 0.04 g |

| AY-3 or AY-3 and SK101 blocked Desmodur N-3300 | |
|---|---|
| Hardener D-1 | Hardener D-2 |
| N-3300 2.9 g, 0.005 mol | N-3300 2.9 g, 0.005 mol |
| AY-3 5.25 g, 0.015 mol | AY-3:SK101 8:2 |
| | AY-3 4.2 g, 0.012 mol |
| | SK101 0.69 g, 0.0003 mol |
| dibutyltin diacetate 0.5%, 0.03 g | dibutyltin diacetate 0.5%, 0.004 g |

TABLE 1

Formulation of Oligoester-diol (1,4-BD)
with Cymel 300 and Different Hardeners C

|  | A | B | C | D | E |
|---|---|---|---|---|---|
| Oligoester-diol | B-440 | B-440 | B-440 | B-440 | B-440 |
| wt (g)/meq. wt | 1.0/4.58 | 1.0/4.58 | 1.0/4.58 | 1.0/4.58 | 1.0/4.58 |
| Hardener | C-1 | C-2 | C-3 | C-4 | C-5 |
| wt (g)/% of total diol | 1.0/100% | 1.0/100% | 1.0/100% | 1.0/100% | 1.0/100% |
| Melamine | Cymel 300 | Cymel 300 | Cymel 300 | Cymel 300 | Cymel 300 |
| wt (g) | 1.45 | 1.45 | 1.45 | 1.45 | 1.45 |
| Leveling | BYK-301 | BYK-301 | BYK-301 | BYK-301 | BYK-301 |
| wt (g) 0.5% | 0.017 | 0.017 | 0.017 | 0.017 | 0.017 |
| DNNDSA wt (g) 0.5% | 0.017 | 0.017 | 0.017 | 0.017 | 0.017 |
| Film Thickness (mil) | 0.9–1.0 | 0.7 | 0.7 | 0.7 | 0.7 |
| D-Impact Rest. | 140 | 140 | 140 | 160 | 160 |
| R-Impact Rest | 100 | 120 | 120 | 160 | 160 |
| Pencil Hardness | 1H | 2H | 2H | 3H | 3H |
| MEK Rub | >200 | >200 | >200 | >200 | >200 |
| Adhesion | 4B–5B | 4B–5B | 4B–5B | 4B–5B | 4B–5B |
| Appearance | Transparent | Transparent | Transparent | Transparent | Transparent w/few slight craters |
| Baking temp/time | 170° C./30 min | 170° C./30 min | 170° C./30 min | 170° C./30 min | 170° C./30 min |

TABLE 2

Formulation of Oligoester-diol (1,4-BD)
with Cymel 300 and Hardener C-4 (different amt of $H_2O$)

|  | F | G | H |
|---|---|---|---|
| Oligoester-diol | B-440 | B-440 | B-440 |
| wt (g)/meq. wt | 10.0/4.58 | 10.0/4.58 | 10.0/4.58 |
| Hardener | C-4 | C-5 | C-4 |
| wt (g)/% of total diol | 10.0/100% | 10.0/100% | 10.0/100% |
| Melamine | Cymel 300 | Cymel 300 | Cymel 300 |
| wt (g) | 10.0 + 45 | 1.0.0 + 45 | 10.0 + 45 |
| Leveling | BYK-301 | BYK-301 | BYK-301 |
| wt (g) 0.5% | 0.17 | 0.17 | 0.17 |
| DNNDSA wt (g) 0.5% | 0.17 | 0.17 | 0.17 |
| $H_2O$ % | — | 5% | 7% |
| Viscosity 2 sec$^{-1}$ 25° C. | 3620 | 1395 | 1280 |
| NVW 110° C. | 92% | 88% | 87% |
| 170° C. | 84% | 79% | 78% |
| Film Thickness (mil) | 0.6 | 0.5–0.6 | 0.6 |
| D-Impact Rest. | 160 | 160 | 160 |
| R-Impact Rest | 140 | 140 | 140 |
| Pencil Hardness | 3H | 3H | 3H |
| MEK Rub | >200 | >200 | >200 |
| Adhesion | 3B | 4B | 4B |
| Appearance | Transparent | Transparent | Transparent |
| Baking temp/time | 170° C./30 min | 170° C./30 min | 170° C./30 min |

TABLE 3

Formulation of Oligoester-diol (1,4-BD)
with Cymel 300 and Hardener D-1 and Hardener D-2

|  | J |
|---|---|
| Oligoester-diol | B-440 |
| wt (g)/meq. wt | 1.0/4.58 |
| Hardener wt (g)/% of total diol | D-1 1.0/100% |
| Melamine wt (g) | Cymel 300 0.45 + 1.0 |
| Leveling wt (g) 0.5% | BYK-301 0.017 |
| DNNDSA wt (g) 0.5% | 0.017 |
| Film Thickness (mil) | 0.6–0.7 |
| D-Impact Rest. | 140 |
| R-Impact Rest | 80 |
| Pencil Hardness | 2H |
| MEK Rub | >200 |
| Adhesion | 5B |
| Appearance | Transparent |
| Baking temp/time | 170° C./30 min |

What is claimed is:

1. A polymeric vehicle comprising:

at least one polyol having an average hydroxyl functionality of from about 1.9 to about 20 hydroxyls per molecule and a number average molecular weight of at least 200;

from about 10 weight percent to about 80 weight percent, based upon the polymeric vehicle, of a phenolic urethane reactive diluent, the phenolic urethane reactive diluent being the reaction product of a compound having an average isocyanate functionality of up to about 20 isocyanate groups per molecule and a phenolic ester alcohol having at least one aliphatic hydroxyl group wherein about one equivalent of isocyanate is reacted with about every equivalent of aliphatic hydroxy group which is a part of the phenolic ester alcohol and wherein the phenolic ester alcohol is the reaction product of a phenol carboxylic acid and an epoxy functional compound, the phenol carboxylic acid having a carboxylic functionality and a hydroxyl group para to one another, the phenol carboxylic acid having not more than one additional substituent on the aromatic phenolic ring additional to the hydroxyl group and the carboxylic acid functionality, the additional substituent selected from the group consisting of hydrogen, halogen, hydroxyl, $C_1$ to $C_8$ alkyl and $C_1$ to $C_8$ alkoxy, the phenolic urethane reactive diluent having at least one unreacted phenolic hydroxyl group and at least two ester groups.

2. A polymeric vehicle as recited in claim 1 wherein the phenolic ester alcohol has at least two ester groups and has the general formula

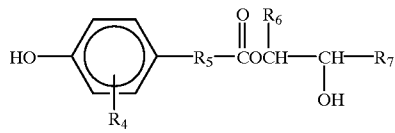

wherein
$R_4$ is selected from the group consisting of hydrogen, halogen, hydroxyl, $C_1$ to $C_8$ alkyl and $C_1$ to $C_8$ alkoxy,
$R_5$ is selected from the group consisting of a direct bond, $C_1$ to $C_{20}$ organic radical having only carbon and hydrogen atoms, and a $C_1$ to $C_{20}$ organic radical which includes in its structure a substitution group selected from the group consisting of phenol, aliphatic hydroxyl, ester, ether, carbonate and combinations thereof,
$R_6$ is selected from the group consisting of hydrogen, a $C_1$ to $C_{20}$ organic radical, and a $C_1$ to $C_{20}$ organic radical which includes in its structure at least one ester linkage or a direct bond which forms with $R_7$ part of a 5 or 6 carbon atom cyclic ring structure,
$R_7$ is $CH_2R_8$ wherein $R_8$ is selected from the group consisting of hydroxy, $OR_9$,

and $R_{11}$,
wherein
$R_9$ is selected from the group consisting of a primary aliphatic group containing 3 to 20 carbon atoms, a secondary aliphatic group containing 3 to 20 carbon atoms, an aromatic group containing 6 to 20 carbon atoms, a primary aliphatic group containing 3 to 20 carbon atoms which includes at least one ester linkage and a secondary aliphatic group containing 3 to 20 carbon atoms which includes at least one ester linkage,
wherein $R_{10}$ is selected from the group consisting of a primary aliphatic group containing 4 to 20 carbon atoms, a secondary aliphatic group containing 4 to 20 carbon atoms, a tertiary aliphatic group containing 4 to 20 carbon atoms, an aromatic group containing 6 to 20 carbon atoms, and combinations thereof, wherein the primary, secondary and tertiary aliphatic groups include at least one ester linkage,
and wherein $R_{11}$ is selected from the group consisting of a $C_2$ to $C_{20}$ organic radical, a $C_2$ to $C_{20}$ organic radical which includes in its structure at least one ester linkage, a $C_2$ to $C_{20}$ organic radical which forms with $R_6$ part of a 5 or 6 carbon atom cyclic ring structure, and combinations thereof.

3. A polymeric vehicle as recited in claim 2 wherein $R_6$ is hydrogen, $R_5$ is a direct bond and $R_4$ is hydrogen.

4. A polymeric vehicle comprising:
a crosslinker selected from the group consisting of a polyfunctional amino resin having an average crosslinking functionality of from about 3 to about 30 crosslinking groups per molecule, a compound having an average isocyanate functionality of from about 1.9 to about 20 isocyanate groups per molecule and mixtures of the polyfunctional amino resin and the polyfunctional isocyanate compound; and
from about 10 weight percent to about 80 weight percent, based upon the weight of the polymeric vehicle, of a phenolic urethane reactive diluent,
the phenolic urethane reactive diluent being the reaction product of a compound having an average isocyanate functionality of up to about 20 isocyanate groups per molecule and a phenolic ester alcohol having at least one aliphatic hydroxyl group wherein about one equivalent of isocyanate is reacted with about every equivalent of aliphatic hydroxy group which is a part of the phenolic ester alcohol, the phenolic urethane reactive diluent having at least one unreacted phenolic hydroxyl group and at least two ester groups and wherein the phenolic ester alcohol is the reaction product of a phenol carboxylic acid and an epoxy functional compound, the phenol carboxylic acid having a carboxylic functionality and a hydroxyl group para to one another, the phenol carboxylic acid having not more than one additional substituent on the aromatic phenolic ring additional to the hydroxyl group and the carboxylic acid functionality, the additional substituent selected from the group consisting of hydrogen, halogen, hydroxyl, C1 to C8 alkyl and C1 to C8 alkoxy.

5. A polymeric vehicle as recited in claim 4, wherein the crosslinker and the reactive diluent are each in amounts effective for reducing VOCs in a formulated coating composition which includes the polymeric vehicle to less than about 3.5 pounds of VOC per gallon of formulated coating composition, the crosslinker and the reactive diluent each in amounts effective for providing a coating binder made from the cured polymeric vehicle with a pencil hardness of at least about HB and an impact resistance of at least about 20-inch pounds direct and at least about 20-inch pounds reverse.

6. The polymeric vehicle as recited in claims 4 or 5, wherein the phenolic ester alcohol has a molecular weight in the range of from about 110 to about 1000 and is the reaction product of a hydroxybenzoic acid and a monoglycidyl compound having a terminal glycidyl group.

7. The polymeric vehicle as recited in claim 6 wherein the hydroxybenzoic acid is parahydroxybenzoic acid and the monoglycidyl compound has the formula

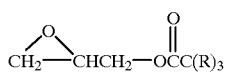

where R represents a mixture of aliphatic groups, the three R groups having a total of 8 carbon atoms.

8. The polymeric vehicle as recited in claims 4 or 5, wherein the phenolic ester alcohol has the general formula

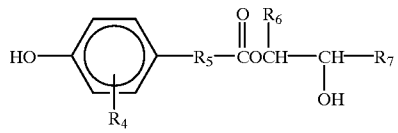

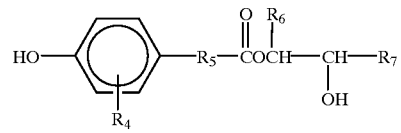

wherein $R_4$ is selected from the group consisting of hydrogen, halogen, hydroxyl, $C_1$ to $C_8$ alkyl and $C_1$ to $C_8$ alkoxy, $R_5$ is selected from the group consisting of a direct bond, $C_1$ to $C_{20}$ organic radical having only carbon and hydrogen atoms, and a $C_1$ to $C_{20}$ organic radical which includes in its structure a substitution group selected from the group consisting of phenol, aliphatic hydroxyl, ester, ether, carbonate and combinations thereof, $R_6$ is selected from the group consisting of hydrogen, a $C_1$ to $C_{20}$ organic radical, and a $C_1$ to $C_{20}$ organic radical which includes in its structure at least one ester linkage or a direct bond which forms with $R_7$ part of a 5 or 6 carbon atom cyclic ring structure, $R_7$ is $CH_2R_8$ wherein $R_8$ is selected from the group consisting of hydroxy, $OR_9$,

and $R_{11}$, wherein $R_5$ is selected from the group consisting of a primary aliphatic group containing 3 to 20 carbon atoms, a secondary aliphatic group containing 3 to 20 carbon atoms, an aromatic group containing 6 to 20 carbon atoms, a primary aliphatic group containing 3 to 20 carbon atoms which includes at least one ester linkage and a secondary aliphatic group containing 3 to 20 carbon atoms which includes at least one ester linkage, wherein $R_{10}$ is selected from the group consisting of a primary aliphatic group containing 4 to 20 carbon atoms, a secondary aliphatic group containing 4 to 20 carbon atoms, a tertiary aliphatic group containing 4 to 20 carbon atoms, an aromatic group containing 6 to 20 carbon atoms, and combinations thereof, wherein the primary, secondary and tertiary aliphatic groups include at least one ester linkage, and wherein $R_{11}$ is selected from the group consisting of a $C_2$ to $C_{20}$ organic radical, a $C_2$ to $C_{20}$, organic radical which includes in its structure at least one ester linkage, a $C_2$ to $C_{20}$ organic radical which forms with $R_6$ part of a 5 or 6 carbon atom cyclic ring structure, and combinations thereof.

9. A polymeric vehicle as recited in claim 8 wherein $R_6$ is hydrogen, $R_5$ is a direct bond and $R_4$ is hydrogen.

10. A phenolic urethane compound which is the reaction product of a compound having an isocyanate functionality of up to about 20 isocyanate groups per molecule and a phenolic ester alcohol having the general formula wherein $R_4$ is selected from the group consisting of hydrogen, halogen, hydroxyl, $C_1$ to $C_8$ alkyl and $C_1$ to $C_5$ alkoxy, $R_5$ is selected from the group consisting of a direct bond, $C_1$ to $C_{20}$ organic radical having only carbon and hydrogen atoms, and a $C_1$ to $C_{20}$ organic radical which includes in its structure a substitution group selected from the group consisting of phenol, aliphatic hydroxyl, ester, ether, carbonate and combinations thereof, $R_6$ is selected from the group consisting of hydrogen, a $C_1$ to $C_{20}$ organic radical, and a $C_1$ to $C_{20}$ organic radical which includes in its structure at least one ester linkage or a direct bond which forms with $R_7$ part of a 5 or 6 carbon atom cyclic ring structure, $R_7$ is $CH_2R_8$ wherein $R_8$ is selected from the group consisting of hydroxy, $OR_9$,

and $R_{11}$, wherein $R_9$ is selected from the group consisting of a primary aliphatic group containing 3 to 20 carbon atoms, a secondary aliphatic group containing 3 to 20 carbon atoms, an aromatic group containing 6 to 20 carbon atoms, a primary aliphatic group containing 3 to 20 carbon atoms which includes at least one ester linkage and a secondary aliphatic group containing 3 to 20 carbon atoms which includes at least one ester linkage, wherein $R_{10}$ is selected from the group consisting of a primary aliphatic group containing 4 to 20 carbon atoms, a secondary aliphatic group containing 4 to 20 carbon atoms, a tertiary aliphatic group containing 4 to 20 carbon atoms, an aromatic group containing 6 to 20 carbon atoms, and combinations thereof, wherein the primary, secondary and tertiary aliphatic groups include at least one ester linkage, and wherein $R_{11}$ is selected from the group consisting of a $C_2$ to $C_{20}$ organic radical, a $C_2$ to $C_{20}$ organic radical which includes in its structure at least one ester linkage, a $C_2$ to $C_{20}$ organic radical which forms with $R_6$ part of a 5 or 6 carbon atom cyclic ring structure, and combinations thereof, the phenolic urethane reactive diluent having at least one unreacted phenolic hydroxyl group.

11. The phenolic urethane compound as recited in claim 10, wherein the isocyanate compound is selected from the group consisting of an isocyanate, a biuret, an isocyanurate and mixtures thereof.

12. A phenolic urethane compound as recited in claim 10 where the compound with the isocyanate functionality has an average isocyanate functionality of from about 2 to about 4.

13. A phenolic urethane compound as recited in claim 10 wherein $R_6$ is hydrogen, $R_5$ is a direct bond and $R_4$ is hydrogen.

14. A phenolic urethane compound as recited in claim 13 where the compound with the isocyanate functionality has an average isocyanate functionality of from about 2 to about 4.

15. A phenolic urethane compound which is the reaction product of a compound having an isocyanate functionality of from about 2 to about 20 isocyanate groups per molecule and a phenolic ester alcohol having at least one aliphatic hydroxyl group and at least two ester linkages, about one equivalent of isocyanate being reacted with about every equivalent of aliphatic hydroxyl group which is a part of the phenolic ester alcohol, the phenolic urethane reactive diluent having at least one unreacted phenolic hydroxyl group and wherein the phenolic ester alcohol is the reaction product of a phenolic carboxylic acid and a glycidyl compound, the phenol carboxylic acid having a carboxylic functionality and a hydroxyl group para to one another, the phenol carboxylic acid having not more than one additional substituent on the aromatic phenol ring additional to the hydroxyl and the carboxylic acid functionality, the additional substituent selected from the group consisting of hydrogen, halogen, hydroxyl, C1 to C8 alkyl and C1 to C8 alkoxy.

16. The phenolic urethane compound as recited in claim 15, wherein the hydroxybenzoic acid is parahydroxybenzoic acid and the glycidyl compound is a monoglycidyl compound which has the formula

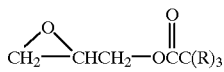

where R represents a mixture of aliphatic groups, the three R groups having a total of 8 carbon atoms.

17. A polymeric vehicle comprising a phenolic urethane compound which has the general formula

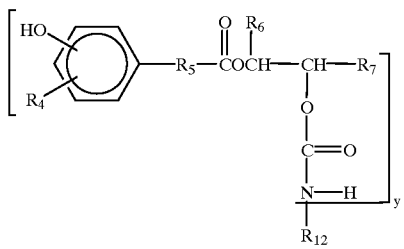

wherein
R$_4$ is selected from the group consisting of hydrogen, halogen, hydroxyl, C$_1$ to C$_8$ alkyl and C$_1$ to C$_8$ alkoxy,
R$_5$ is selected from the group consisting of a direct bond, C$_1$ to C$_{20}$ organic radical having only carbon and hydrogen atoms, and a C$_1$ to C$_{20}$ organic radical which includes in its structure a substitution group selected from the group consisting of phenol, aliphatic hydroxyl, ester, ether, carbonate and combinations thereof,
R$_6$ is selected from the group consisting of hydrogen, a C$_1$ to C$_{20}$ organic radical, and a C$_1$ to C$_{20}$ organic radical which includes in its structure at least one ester linkage or a direct bond which forms with R$_7$ part of a 5 or 6 carbon atom cyclic ring structure,
R$_7$ is CH$_2$R$_8$ wherein R$_8$ is selected from the group consisting of hydroxy, OR$_8$,

and R$_{11}$, wherein R$_9$ is selected from the group consisting of a primary aliphatic group containing 3 to 20 carbon atoms, a secondary aliphatic group containing 3 to 20 carbon atoms, an aromatic group containing 6 to 20 carbon atoms, a primary aliphatic group containing 3 to 20 carbon atoms which includes at least one ester linkage and a secondary aliphatic group containing 3 to 20 carbon atoms which includes at least one ester linkage, wherein R$_{10}$ is selected from the group consisting of a primary aliphatic group containing 4 to 20 carbon atoms, a secondary aliphatic group containing 4 to 20 carbon atoms, a tertiary aliphatic group containing 4 to 20 carbon atoms, an aromatic group containing 6 to 20 carbon atoms, and combinations thereof, wherein the primary, secondary and tertiary aliphatic groups include at least one ester linkage, and wherein R$_{11}$ is selected from the group consisting of a C$_2$ to C$_{20}$ organic radical, a C$_2$ to C$_{20}$ organic radical which includes in its structure at least one ester linkage, a C$_2$ to C$_{20}$ organic radical which forms with R$_6$ part of a 5 or 6 carbon atom cyclic ring structure, and combinations thereof, wherein y is about 1 to about 4, and where R$_{12}$ is selected from the group consisting of alkyl, an alkyl difunctional radical, alkenyl, alkenyl difunctional radical, aromatic and an aromatic difunctional radical.

18. The polymeric vehicle as recited in claim 17, where R$_{12}$ is selected from the group consisting of

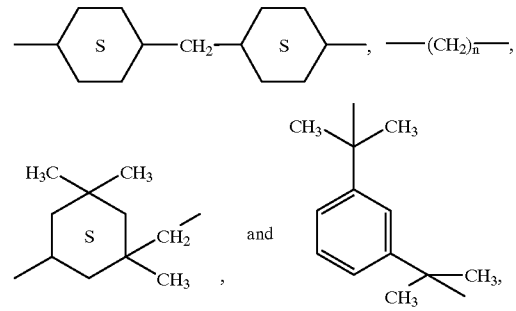

wherein n is greater than 1.

19. A polymeric vehicle as recited in claim 17 or 18 wherein the phenolic reactive diluent has the general formula

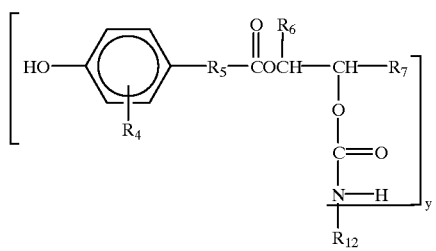

where y=2 or 3, and where $R_{12}$ is selected from the group consisting of alkyl, an alkyl difunctional radical, alkenyl, alkenyl difunctional radical, aromatic and an aromatic difunctional radical and wherein the molecular weight of the phenolic reactive diluent is not more than 50,000.

20. The polymeric vehicle as recited in claim 18, wherein the phenolic urethane reactive diluent has the formula

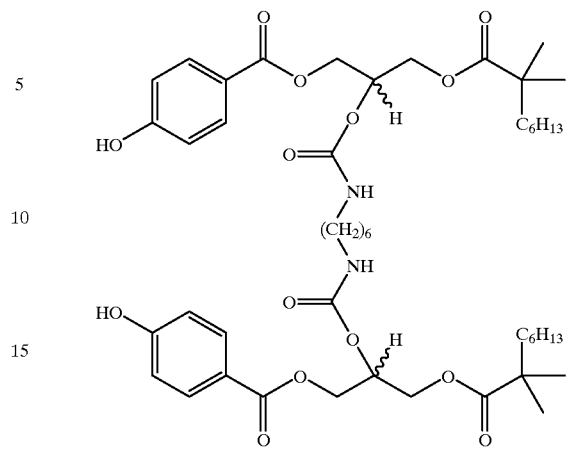

21. The polymeric vehicle as recited in claim 18, wherein the phenolic urethane reactive diluent has the formula

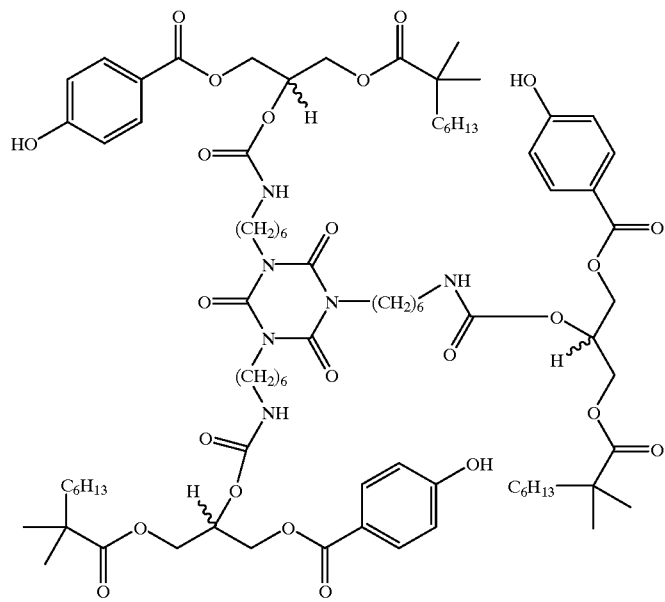

22. A polymeric vehicle as recited in claims 18, 20, or 21, wherein the polymeric vehicle further comprises a compound having an isocyanate functionality of from about 1.9 to about 20 isocyanate groups per molecule.

23. A polymeric vehicle as recited in claim 17 wherein $R_6$ is hydrogen, $R_5$ is a direct bond and $R_4$ is hydrogen.

24. The polymeric vehicle as recited in claim 17 wherein $R_{12}$ is selected from the group consisting of

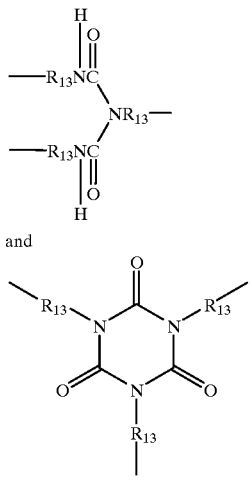

and $R_{13}$ is a difunctional radical selected from the group consisting of an alkyl difunctional radical, alkenyl difunctional and aromatic difunctional radical.

25. A polymeric vehicle which comprises;

a phenolic urethane reactive diluent;

at least one polyol having an average hydroxyl functionality of from about 1.9 to about 20 hydroxyls per molecule and a number average molecular weight of at least 200; and the phenolic urethane reactive diluent having the general formula

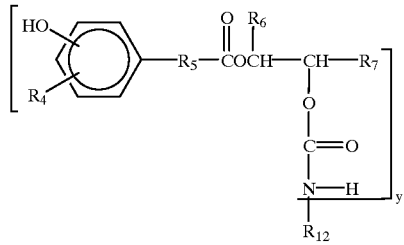

wherein $R_4$ is selected from the group consisting of hydrogen, halogen, hydroxyl, $C_1$ to $C_8$ alkyl and $C_1$ to $C_8$ alkoxy, $R_5$ is selected from the group consisting of a direct bond, $C_1$ to $C_{20}$ organic radical having only carbon and hydrogen atoms, and a $C_1$ to $C_{20}$ organic radical which includes in its structure a substitution group selected from the group consisting of phenol, aliphatic hydroxyl, ester, ether, carbonate and combinations thereof, $R_6$ is selected from the group consisting of hydrogen, a $C_1$ to $C_{20}$ organic radical, and a $C_1$ to $C_{20}$ organic radical which includes in its structure at least one ester linkage or a direct bond which forms with $R_7$ part of a 5 or 6 carbon atom cyclic ring structure, $R_7$ is $CH_2R_8$ wherein $R_8$ is selected from the group consisting of hydroxy, $OR_9$,

and $R_{11}$, wherein $R_9$ is selected from the group consisting of a primary aliphatic group containing 3 to 20 carbon atoms, a secondary aliphatic group containing 3 to 20 carbon atoms, an aromatic group containing 6 to 20 carbon atoms, a primary aliphatic group containing 3 to 20 carbon atoms which includes at least one ester linkage and a secondary aliphatic group containing 3 to 20 carbon atoms which includes at least one ester linkage, wherein $R_{10}$ is selected from the group consisting of a primary aliphatic group containing 4 to 20 carbon atoms, a secondary aliphatic group containing 4 to 20 carbon atoms, a tertiary aliphatic group containing 4 to 20 carbon atoms, an aromatic group containing 6 to 20 carbon atoms, and combinations thereof, wherein the primary, secondary and tertiary aliphatic groups include at least one ester linkage, and wherein $R_{11}$ is selected from the group consisting of a $C_2$ to $C_{20}$ organic radical, a $C_2$ to $C_{20}$ organic radical which includes in its structure at least one ester linkage, a $C_2$ to $C_{20}$ organic radical which forms with $R_6$ part of a 5 or 6 carbon atom cyclic ring structure, and combinations thereof, wherein y is about 1 to about 4, and where $R_{12}$ is selected from the group consisting of alkyl, an alkyl difunctional radical, alkenyl, alkenyl difunctional radical, aromatic and an aromatic difunctional radical.

26. A polymeric vehicle as recited in claim 25 wherein the phenolic reactive diluent has the general formula

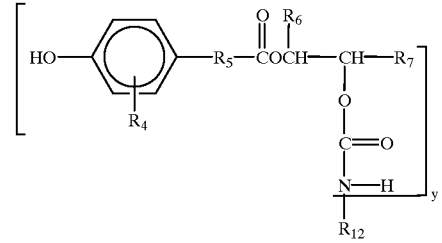

wherein y=2 or 3, and where $R_{12}$ is selected from the group consisting of alkyl, an alkyl difunctional radical, alkenyl, alkenyl difunctional radical, aromatic and an aromatic difunctional radical and wherein the molecular weight of the phenolic reactive diluent is not more than 50,000.

27. A polymeric vehicle as recited in claim 25, wherein y=2 to 3.

28. A polymeric vehicle as recited in claim 27 wherein the polymeric vehicle comprises at least about 10 weight percent phenolic reactive diluent, based upon the weight of the polymeric vehicle.

29. A polymeric vehicle as recited in claim 27 or 28 wherein the phenolic reactive diluent has the general formula

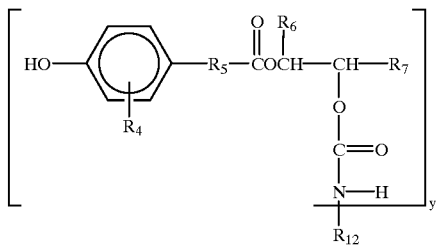

where y=2 or 3, and where $R_{12}$ is selected from the group consisting of alkyl, an alkyl difunctional radical, alkenyl, alkenyl difunctional radical, aromatic and an aromatic difunctional radical and wherein the molecular weight of the phenolic reactive diluent is not more than 50,000.

30. A polymeric vehicle as recited in claims 25, 26, 27, or 28 wherein the phenolic reactive diluent has a molecular weight of not more than about 2,000.

31. A polymeric vehicle as recited in claim 30 wherein the polymeric vehicle further includes a crosslinker blend which comprises at least one isocyanate compound selected from the group consisting of an isocyanate, a biuret, an isocyanurate and mixtures thereof; and at least one amino resin.

32. A polymeric vehicle as recited in claims 25, 27 or 28 wherein the polymeric vehicle further includes a crosslinker blend which comprises at least one isocyanate compound selected from the group consisting of an isocyanate, a biuret, an isocyanurate and mixtures thereof; and at least one amino resin.

33. The polymeric vehicle as recited in claim 25, wherein the polymeric vehicle further includes a diphenolic hardener.

34. The polymeric vehicle as recited in claim 25, wherein $R_{12}$ is a difunctional radical and the difunctional radical is selected from the group consisting of

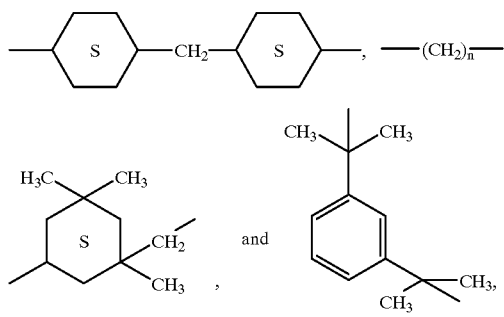

wherein n is greater than 1.

35. A polymeric vehicle as recited in claim 25 wherein $R_6$ is hydrogen, $R_5$ is a direct bond and $R_4$ is hydrogen.

36. The polymeric vehicle as recited in claim 25 wherein $R_{12}$ is selected from the group consisting of

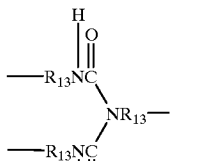

and

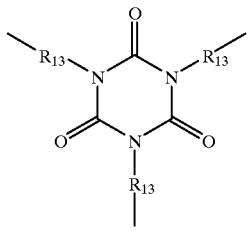

and $R_{13}$ is a difunctional radical selected from the group consisting of an alkyl difunctional radical, alkenyl difunctional and aromatic difunctional radical.

37. The polymeric vehicle as recited in claim 25, wherein the polyol is selected from the group consisting of a polyester polymer, an acrylic polymer, an alkyd polymer, and epoxy polymer and mixtures thereof.

38. The polymeric vehicle as recited in claim 25, wherein the polyol is a polyester polymer having a number average molecular weight in the range of from about 200 to about 20,000.

39. The polymeric vehicle as recited in claim 25, wherein the polyol is an acrylic polymer having a number average molecular weight in the range of from about 300 to about 5,000.

40. The polymeric vehicle as recited in claim 25, wherein the polyol is an alkyd polymer having a number average molecular weight in the range of from about 500 to about 20,000.

41. The polymeric vehicle as recited in claim 25, wherein the polyol is an epoxy polymer having a number average molecular weight in the range of from about 500 to about 6,000.

42. The polymeric vehicle as recited in claim 25, wherein the polyol is a polyester having number average molecular weight of from about 200 to about 20,000 and wherein the phenolic urethane reactive diluent has a molecular weight in the range of from about 240 to about 1140.

43. The polymeric vehicle as recited in claim 25, wherein the polyol is an acrylic polymer having a number average molecular weight of from about 300 to about 5,000 and wherein the phenolic urethane reactive diluent has a molecular weight in the range of from about 240 to about 1140.

44. The polymeric vehicle as recited in claim 25, wherein the polyol is an alkyd polymer having a number average molecular weight of from about 500 to about 20,000 and wherein the phenolic urethane reactive diluent has a molecular weight in the range of from about 240 to about 1140.

45. The polymeric vehicle as recited in claim 25, wherein the polyol is an epoxy polymer having a number average molecular weight of from about 500 to about 6,000 and wherein the phenolic urethane reactive diluent has a molecular weight in the range of from about 240 to about 1140.

46. A polymeric vehicle as recited in claim 25, wherein the polymeric vehicle further includes a crosslinker and the crosslinker, the polyol and the phenolic reactive diluent are each in respective amounts for providing a coating binder made from the cured polymeric vehicle with a pencil hardness of at least about HB and an impact resistance of at least 30-inch pounds direct and at least about 30-inch pounds reverse.

47. The polymeric vehicle as recited in claim 46, wherein the polyol is a polyester having a number average molecular weight of from about 200 to about 20,000.

48. The polymeric vehicle as recited in claim 46, wherein the polyol is an acrylic polymer having a number average molecular weight of from about 300 to about 5,000.

49. The polymeric vehicle as recited in claim 46, wherein the polyol is an alkyd polymer having a number average molecular weight of from about 500 to about 6,000.

50. The polymeric vehicle as recited in claim 46, wherein the polyol is an epoxy polymer having a number average molecular weight of from about 500 to about 6,000.

51. A polymeric vehicle which comprises:

from about 10 weight percent to about 80 weight percent phenolic urethane reactive diluent, based upon the weight of the polymeric vehicle;

at least one polyol having an average hydroxyl functionality of from about 1.9 to about 20 hydroxyls per molecule and a number average molecular weight of at least 200; and the phenolic urethane reactive diluent having the general formula

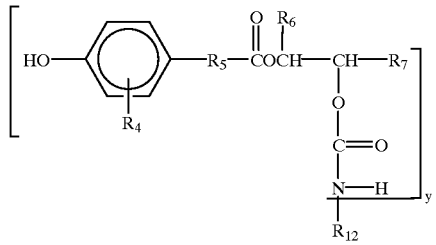

wherein
$R_4$ is selected from the group consisting of hydrogen, halogen, hydroxyl, $C_1$ to $C_8$ alkyl and $C_1$ to $C_8$ alkoxy, $R_5$ is selected from the group consisting of a direct bond, $C_1$ to $C_{20}$ organic radical having only carbon and hydrogen atoms, and a $C_1$ to $C_{20}$ organic radical which includes in its structure a substitution group selected from the group consisting of phenol, aliphatic hydroxyl, ester, ether, carbonate and combinations thereof, $R_6$ is selected from the group consisting of hydrogen, a $C_1$ to $C_{20}$ organic radical, and a $C_1$ to $C_{20}$ organic radical which includes in its structure at least one ester linkage or a direct bond which forms with $R_7$ part of a 5 or 6 carbon atom cyclic ring structure, $R_7$ is $CH_2R_8$ wherein $R_8$ is selected from the group consisting of hydroxy,

and $R_{11}$,
wherein
$R_9$ is selected from the group consisting of a primary aliphatic group containing 3 to 20 carbon atoms, a secondary aliphatic group containing 3 to 20 carbon atoms, an aromatic group containing 6 to 20 carbon atoms, a primary aliphatic group containing 3 to 20 carbon atoms which includes at least one ester linkage and a secondary aliphatic group containing 3 to 20 carbon atoms which includes at least one ester linkage, wherein $R_{10}$ is selected from the group consisting of a primary aliphatic group containing 4 to 20 carbon atoms, a secondary aliphatic group containing 4 to 20 carbon atoms, a tertiary aliphatic group containing 4 to 20 carbon atoms, an aromatic group containing 6 to 20 carbon atoms, and combinations thereof, wherein the primary, secondary and tertiary aliphatic groups include at least one ester linkage, and wherein $R_{11}$ is selected from the group consisting of a $C_2$ to $C_{20}$ organic radical, a $C_2$ to $C_{20}$ organic radical which includes in its structure at least one ester linkage, a $C_2$ to $C_{20}$ organic radical which forms with $R_6$ part of a 5 or 6 carbon atom cyclic ring structure, and combinations thereof, where y=2 or 3, and where $R_{12}$ is selected from the group consisting of alkyl, an alkyl difunctional radical, alkenyl, alkenyl difunctional radical, aromatic and an aromatic difunctional radical and wherein the molecular weight of the phenolic reactive diluent is not more than 50,000.

52. A polymeric vehicle as recited in claim 51 wherein the phenolic reactive diluent has a molecular weight of not more than about 2,000.

53. The polymeric vehicle as recited in claim 51, wherein $R_{12}$ is a difunctional radical and the difunctional radical is selected from the group consisting of

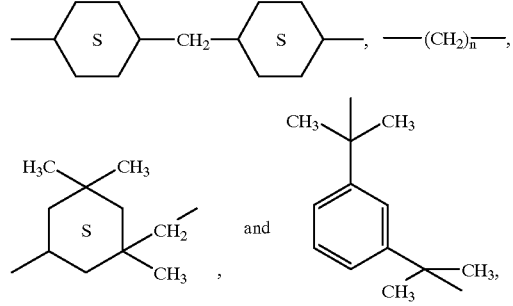

wherein n is greater than 1.

54. A polymeric vehicle as recited in claim 51 wherein the polymeric vehicle further includes a crosslinker blend which comprises at least one isocyanate compound selected from the group consisting of an isocyanate, a biuret, an isocyanurate and mixtures thereof and at least one amino resin.

55. A polymeric vehicle as recited in claim 51 wherein $R_6$ is hydrogen, $R_5$ is a direct bond and $R_4$ is hydrogen.

56. The polymeric vehicle as recited in claim 51 wherein $R_{12}$ is selected from the group consisting of

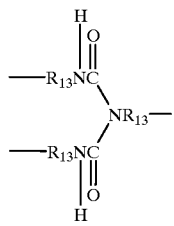
-continued
and
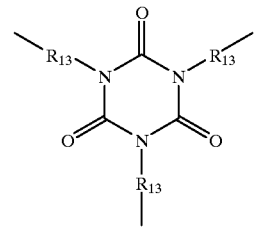
and $R_{13}$ is a difunctional radical selected from the group consisting of an alkyl difunctional radical, alkenyl difunctional and aromatic difunctional radical.
* * * * *